United States Patent
Anzenbacher, Jr. et al.

(10) Patent No.: US 8,785,002 B1
(45) Date of Patent: Jul. 22, 2014

(54) HIGH-ENERGY TRIPLET HOST MATERIALS, LUMINESCENT LAYER COMPRISING THE SAME, AND ORGANIC ELECTROLUMINESCENT DEVICE COMPRISING THE LUMINESCENT LAYER

(75) Inventors: Pavel Anzenbacher, Jr., Bowling Green, OH (US); Shin-ya Takizawa, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 433 days.

(21) Appl. No.: 12/381,247

(22) Filed: Mar. 10, 2009

Related U.S. Application Data

(60) Provisional application No. 61/195,388, filed on Oct. 7, 2008.

(51) Int. Cl.
*H01L 51/00* (2006.01)
*C07D 235/18* (2006.01)

(52) U.S. Cl.
USPC ........... 428/690; 428/917; 313/504; 313/506; 548/302.7; 252/301.16

(58) Field of Classification Search
None
See application file for complete search history.

(56) References Cited

U.S. PATENT DOCUMENTS

| | | | |
|---|---|---|---|
| 5,645,948 A * | 7/1997 | Shi et al. | 428/690 |
| 6,838,194 B2 * | 1/2005 | Huang et al. | 428/690 |
| 2002/0037427 A1 * | 3/2002 | Taguchi | 428/690 |
| 2003/0146443 A1 * | 8/2003 | Yamazaki et al. | 257/80 |
| 2006/0134460 A1 * | 6/2006 | Kondakova et al. | 428/690 |
| 2006/0163562 A1 * | 7/2006 | Boerner | 257/40 |
| 2007/0099025 A1 * | 5/2007 | Oshiyama et al. | 428/690 |
| 2007/0104976 A1 | 5/2007 | Iwakuma et al. | |
| 2007/0111027 A1 * | 5/2007 | Chen et al. | 428/690 |
| 2009/0167166 A1 | 7/2009 | Bach et al. | |
| 2009/0188547 A1 * | 7/2009 | Hayashi et al. | 136/249 |
| 2010/0231123 A1 | 9/2010 | Otsu et al. | |
| 2010/0295026 A1 | 11/2010 | Tsuji et al. | |

FOREIGN PATENT DOCUMENTS

| | | | |
|---|---|---|---|
| EP | 1651013 | * | 4/2006 |
| JP | 2004-300301 | * | 10/2004 |
| WO | WO 2007055186 A1 | | 5/2007 |
| WO | WO 2007108459 A1 | | 9/2007 |
| WO | WO 2007137725 A1 | | 12/2007 |

OTHER PUBLICATIONS

Nomura et al., Synthetic Metals, 151, (2005), pp. 261-268.*
Takizawa et al., Chemistry of Materials, (2009), vol. 29, pp. 2452-2458.*

* cited by examiner

*Primary Examiner* — Dawn Garrett
(74) *Attorney, Agent, or Firm* — Marshall & Melhorn, LLC

(57) ABSTRACT

The present invention includes high triplet energy compositions of matter, methods of their manufacture, devices incorporating the compositions of matter, and methods of using those compositions of matter and devices. The devices incorporating the high triplet energy compositions of matter include electroluminescence devices including organic light-emitting diodes (OLEDs). The present invention also includes methods of using the compositions of matter, such as by operating the devices of the present invention incorporating them, to provide light through electroluminescence, as well as obtaining and/or operating devices of the present invention through the application of electrical energy or potential, as well as methods of providing light through electroluminescence through their operation.

8 Claims, 11 Drawing Sheets

HIGH-ENERGY TRIPLET HOST MATERIALS, LUMINESCENT LAYER COMPRISING THE SAME, AND ORGANIC ELECTROLUMINESCENT DEVICE COMPRISING THE LUMINESCENT LAYER

RELATED APPLICATION DATA

This application claims the priority benefit of U.S. Provisional Application Ser. No. 61/195,388, filed Oct. 7, 2008, which is hereby incorporated in its entirety herein by reference.

FIELD OF THE INVENTION

The present invention relates to efficient organic light emitting devices (OLEDs), and more specifically to the organic semiconductors capable of hosting luminescent emitters used in such devices. More specifically, the present invention relates to organic semiconductors that display high energy triplet states and may be used to fabricate blue phosphorescent emissive layers with improved stability and efficiency when incorporated into an OLED.

BACKGROUND

Opto-electronic devices that make use of organic luminescent materials are becoming increasingly desirable for a number of reasons. The organic semiconductor materials found application in inexpensive fabrication processes for organic opto-electronic devices. Such materials and devices have the potential for cost advantages over semiconductor-based inorganic devices. In addition, the inherent properties of organic and organic materials, such as their flexibility, may make them well suited for particular applications such as fabrication on a flexible substrate. Example of organic optoelectronic devices include organic light emitting devices (OLEDs), where the organic materials may have performance advantages over conventional materials. For example, the wavelength at which an organic emissive layer emits light may generally be readily timed with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a luminescent or phosphorescent small molecule emitter. These variations are alos included in the present invention.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. In a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices where both electrodes are transparent may also be fabricated. Side emitting OLEDs comprising one or both electrodes may be opaque or reflective in such devices may also be fabricated.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between. Accordingly, it will be understood that the invention encompasses any OLED that comprises layers and constituents which are arranged so as to provide a functional OLED, regardless the specific arrangement or orientation of the layers or the device comprising them.

As used herein, "dopant" means a luminescent materials or compound capable of emitting light of a desired wavelength, but is generally (but not always) capable or intended to transport electrical charge. Such dopant is usually dispersed in a host material, which is capable of transporting the charges under a bias voltage.

As used herein, "host" means material, which is generally (but not always) essentially colorless transparent non-emissive organic semiconductor material capable of transporting electrical charge under bias voltage.

The host capable of transporting negative charge is a semiconductor capable of accepting electrons from adjacent layer thus becoming negatively charged. Said negative charge migrates toward anode through the host material under bias voltage. The host capable of transporting positive charge is a semiconductor capable of accepting holes (an equivalent of cation) from adjacent layer thus becoming positively charged.

A bipolar or ambipolar host is a semiconductor capable of accepting both electrons and holes from adjacent layer thus becoming locally negatively and positively charged. The overall charge in the bipolar hosts may be positive if the prevalent charge carrier is a hole, or negative if the prevalent charge carrier is an electron.

As used herein, "doped emissive layer" means material, in which the emissive dopant is dispersed in a host to form a semiconducting blend capable of both transporting the electrical charge under bias as well as emitting light of a desired wavelength that corresponds to the dopant emission spectrum.

One application for luminescent emissive layers is a full color display. Industry standards for such a display call for pixels adapted to emit particular colors, referred to as "saturated" colors. In particular, these standards call for saturated red, green, and blue pixels. Color may be measured using CIE coordinates or $CR_1$, which are well known to the art.

Industry standards call for the lifetime of such full color displays to be at least about 5000 hours. In addition, high stability and efficiency are important characteristics of high quality displays. These requirements generate a need for organic semiconductor materials useful for fabrication OLEDs exhibiting longer lifetimes, higher stability, and higher efficiency in the red, green and blue wavelength regimes than have been achieved in the prior art.

One example of a host capable of transporting electrons is 1,3,5-tris(phenyl-2-benzimidazolyl)benzene, denoted TPBI, which has the structure of Formula I:

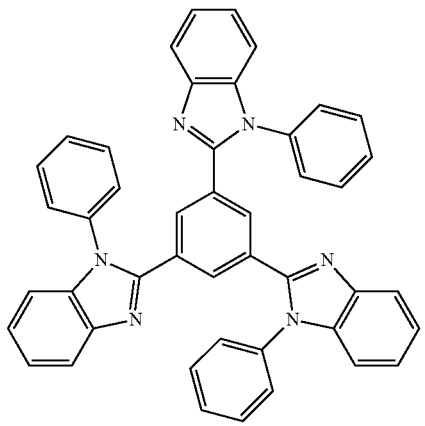

I

TPBI displays an fluorescence and phosphorescence spectra shown in FIG. 3 corresponding to a triplet energy of $_3E=2.67$ eV respectively. Shi, J.; Tang, C. W.; Chen, C. H. U.S. Pat. No. 5,646,948, 1997. Gao, Zhiqiang; Lee, C. S.; Bello, I.; Lee, S. T.; Chen, Ruey-Ming; Luh, Tien-Yau; Shi, J.; Tang, C. W. *Appl. Phys. Lett.* 1999, 74, 865. The unique nature of TPBI provides also for high electron mobility and thermal stability. Wong, T. C.; Kovac, J.; Lee, C. S.; Hung, L. S.; Lee, S. T. *Chem. Phys. Lett.* 2001, 334, 61.

Second example of a host capable of transporting electrons is N,N'-dicarbazolyl-4,4'-biphenyl, denoted CBP, which has the structure of Formula II:

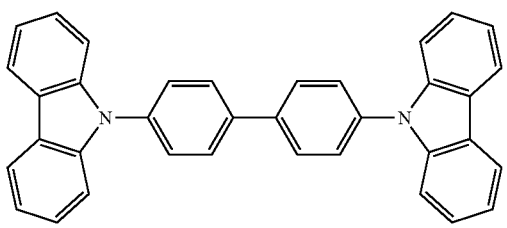

II

CBP displays an fluorescence and phosphorescence spectra corresponding to the triplet energy of $_3E=2.56$ eV respectively. This compound is known in the literature since 1950's. Gilman, H.; Honeycutt, J. B., Jr. *J. Org. Chem.* 1957, 22, 226. Patented for use in organic electroluminescence Kanai, H.; Sato, Y.; Ichinosawa, A. Jpn. Kokai Tokkyo Koho 1996, JP 08060144. It's use is also described in Adachi, C.; Kwong, R. C.; Djurovich, P.; Adamovich, V.; Baldo, M. A.; Thompson, M. E.; Forrest, S. R. *Appl. Phys. Lett.* 2001, 79, 2082. The unique nature of CBP provides also for high hole mobility and thermal stability. Parshin, M. A.; Ollevier, J.; Van der Auweraer, M. *Proc. SPIE* 2006, 6192, 61922A/1-61922A/8.

Since triplets and singlets are generated by electron-hole recombination in a 3:1 ratio, utilizing triplet excited states generated in the host materials by phosphorescent dopants is of utmost importance for obtaining the maximum light output in OLEDs. Baldo, M. A. and Forrest, S. R. *Phys. Rev. B.* 2000, 62, 10958. Adachi, C. et al. *Appl. Phys. Lett.* 2001, 79, 2082.

In general, the desired energy of singlet and triplet energy transfer in the emissive layer is from the non-emissive host to the emissive dopant. Therefore the excited state energy of the host should be higher than that of the dopant. This is generally (but not always) valid for both singlet and triplet excitons. Given the predominance of the triplet excitons generated in the OLEDs, to obtain a device with high luminant efficiency, the triplet energy of organic hosts should be higher than that of the dopant to encourage an exothermic energy transfer from the host to the dopant.

To fabricate emissive layers and corresponding OLEDs using blue and blue-green phosphorescent dopant-emitters such as Ir or Pt complexes requires hosts with high triplet energies ($_3E=2.7$ eV) to achieve an exothermic energy transfer from the host to dopant and prevent back-transfer from the dopant to the host.

An example of a blue-emitting dopant utilizing Ir(III) center is iridium(III)bis[(4,6-difluorophenyl)-pyridinato-$N,C_2$] picolinate, denoted FIrpic, which has the structure of Formula III:

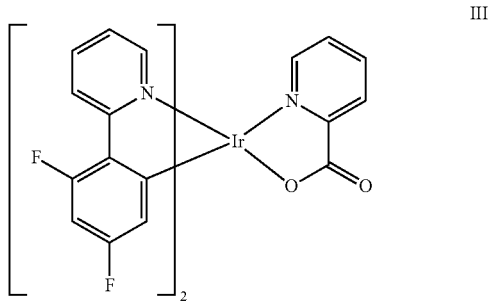

III

FIrpic displays a blue phosphorescence spectra corresponding to a triplet energies of $_3E=2.65$ eV. D'Andrade, B; Thompson, M. E.; Forrest, S. R. PCT Int. Appl. 2002, WO 2002091814; Tokito, S.; Iijima, T.; Suzuki, Y.; Kita, H.; Tsuzuki, T.; Sato, F. *Appl. Phys. Lett.* 2003, 83, 569.

From the comparison of triplet energies of CBP ($_3E=2.56$ eV) and FIrpic ($_3E=2.65$ eV) it appears that an emissive layer composed of CBP host and FIrpic dopant that the triplet energy transfer is likely to occur from the FIrpic dopant to the CBP host, which is not desirable as the triplet excitons partly migrate away from the emissive dopant.

Currently, the successful application of dopants that display deep-blue phosphorescence is partly precluded by an insufficient availability of hosts that display high triplet levels ($_3E>2.70$ eV).

SUMMARY OF THE INVENTION

The present invention includes compositions of matter, methods of their manufacture, devices incorporating the compositions of matter, and methods of using those compositions of matter and devices.

Organic light emitting devices (OLEDs) comprising host material displaying high-triplet energy for improved emissive and host charge-transport properties are provided.

The host materials display improved charge transport properties and high energy of singlet and triplet excited states.

The provided light emitting device comprises an anode, a cathode, and an emissive layer disposed between the anode and the cathode. The emissive layer comprises an emissive material and a host material having the structure described by Formula IV:

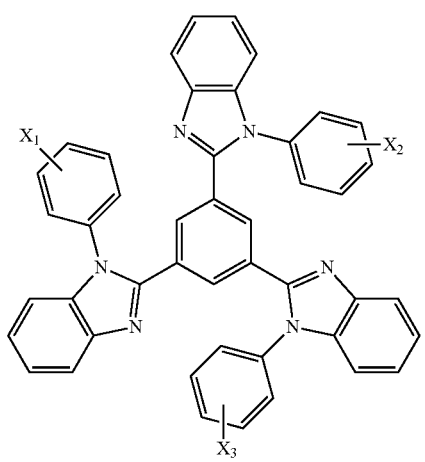

IV wherein $X_1$ is a substituent selected from the group consisting of H, CN, $CO_2R$, C(O)R, $NR_2$, $NAr_2$, OR, SR, SOR, $SO_2R$, $SO_3H$, $SO_2NR_1R_2$, $B(OH)_2$, $B(OR_1)(OR_2)$, halo, alkyl, fluoroalkyl, fluoroalkenyl, fluoroalkynyl, aryl, heteroaryl or heterocyclic group, wherein said alkyl, alkylaryl, alkenyl, alkenylaryl, alkynyl, alkynylaryl, aryl, heteroaryl or heterocyclic group is unsubstituted or optionally, substituted;

$X_2$ is a substituent selected from the group consisting of H, CN, $CO_2R$, C(O)R, $NR_2$, $NAr_2$, OR, SR, SOR, $SO_2R$, $SO_3H$, $SO_2NR_1R_2$, $B(OH)_2$, $B(OR_1)(OR_2)$, halo, alkyl, fluoroalkyl, fluoroalkenyl, fluoroalkynyl, aryl, heteroaryl or heterocyclic group, wherein said alkyl, alkylaryl, alkenyl, alkenylaryl, alkynyl, alkynylaryl, aryl, heteroaryl or heterocyclic group is unsubstituted or optionally, substituted;

$X_3$ is a substituent selected from the group consisting of H, CN, $CO_2R$, C(O)R, $NR_2$, $NAr_2$, OR, SR, SOR, $SO_2R$, $SO_3H$, $SO_2NR_1R_2$, $B(OH)_2$, $B(OR_1)(OR_2)$, halo, alkyl, fluoroalkyl, fluoroalkenyl, fluoroalkynyl, aryl, heteroaryl or heterocyclic group, wherein said alkyl, alkylaryl, alkenyl, alkenylaryl, alkynyl, alkynylaryl, aryl, heteroaryl or heterocyclic group is unsubstituted or optionally, substituted;

each R is independently selected from H, alkyl, alkylaryl and aryl.

The provided light emitting device comprises an anode, a cathode, and an emissive layer disposed between the anode and the cathode. The emissive layer comprises an emissive material and a host material having the structure described by Formula V:

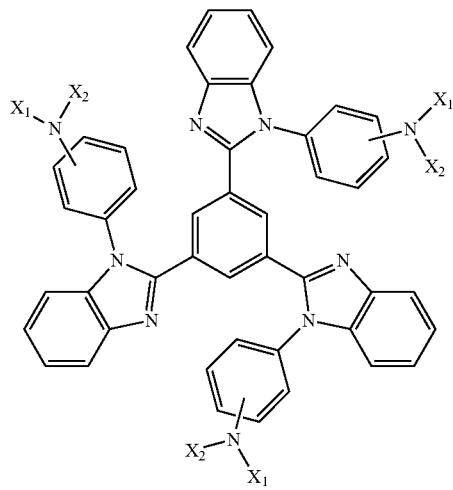

V wherein $X_1$ is a substituent selected from the group consisting of alkyl, aryl, heteroaryl or heterocyclic group, wherein said alkyl, aryl, heteroaryl or heterocyclic group is unsubstituted or optionally, substituted;

$X_2$ is a substituent selected from the group consisting of alkyl, aryl, heteroaryl or heterocyclic group, wherein said alkyl, aryl, heteroaryl or heterocyclic group is unsubstituted or optionally, substituted;

The provided light emitting device comprises an anode, a cathode, and an emissive layer disposed between the anode and the cathode. The emissive layer comprises an emissive material and a host material having the structure described by Formula VI:

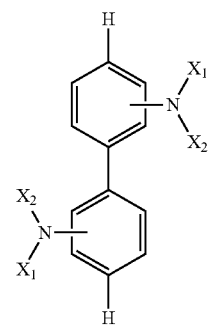

VI wherein $X_1$ is a substituent selected from the group consisting of alkyl, aryl, heteroaryl or heterocyclic group, wherein said alkyl, aryl, heteroaryl or heterocyclic group is unsubstituted or optionally, substituted;

$X_2$ is a substituent selected from the group consisting of alkyl, aryl, heteroaryl or heterocyclic group, wherein said alkyl, aryl, heteroaryl or heterocyclic group is unsubstituted or optionally, substituted;

The emissive layer itself is also provided. The emissive layer comprises the host material according to this invention and a suitable dopant. The emissive layer may have improved charge transport capabilities, provide higher current density, electroluminescent efficiency, stability, singlet level energies, triplet level energies thereby able to act as a charge transporting light-emissive layer when incorporated into a light emitting device.

Additionally, the devices of the present invention are expected to exhibit improved efficiency while being easily fabricated.

The present invention also includes methods of using the compositions of matter, such as by operating the devices of the present invention incorporating them, to provide light through electroluminescence. The present invention accordingly includes obtaining and/or operating devices of the present invention through the application of electrical energy or potential, as well as methods of providing light through electroluminescence.

DETAILED DESCRIPTION

Figure 1:
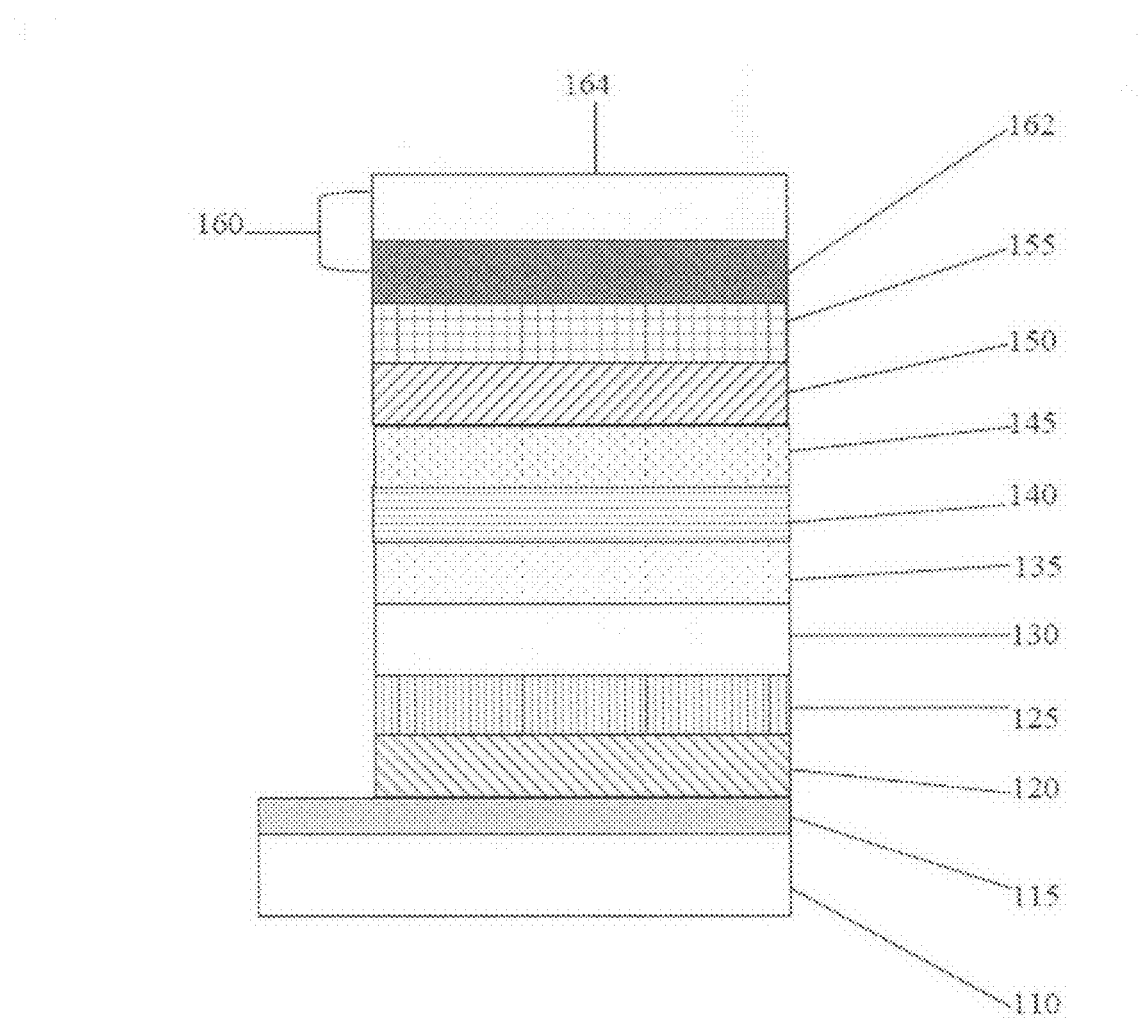
FIG. 1 shows an organic light emitting device having separate emissive, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole recombine on the same molecule, an "exciton," which is a localized electron-hole pair having an excited state energy, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("luminescence") as disclosed, for example, in U.S. Pat. No. 4,769,292, which is incorporated by reference in its entirety. Luminescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices", Nature 1998, 395, 151; and Baldo et al., "Very highefficiency green organic light-emitting devices based on electrophosphorescence", Appl. Phys. Lett., 1999, 75, 4, which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. An example of a molecule exhibiting phosphorescence at room temperature is FIrpic.

Generally, the excitons in an OLED are believed to be created in a ratio of about 3:1, i.e., approximately 75% triplets and 25% singlets. See, Adachi et al., "Nearly 100% Internal Phosphorescent Efficiency in an Organic Light Emitting Device," J. Appl. Phys. 2001, 90, 5048, which is incorporated by reference in its entirety, although this theory is not limiting to the present invention. In a fluorescence-only device, the energy of triplet excitons is generally lost to radiationless decay processes and are not utilized for generation of light. In many cases, singlet excitons may readily transfer their energy to triplet excited states via "intersystem crossing," whereas triplet excitons may not readily transfer their energy to singlet excited states. In the case of OLEDs utilizing triplet emitters, the 100% internal quantum efficiency is theoretically possible. OLEDs utilizing phosphorescent materials that emit from triplet excited states are disclosed, for example, in U.S. Pat. No. 6,303,238, which is incorporated by reference in its entirety.

Phosphorescence from a triplet emitter may be preceded by an energy transfer from a singlet excited state of another molecule located in the close vicinity of the triplet emitter. Thus the hole electron recombination may produce singlet and triplet excitons on one molecule followed by energy transfer of singlet, triplet or both singlet and triplet excitons to the triplet emitter. The material serving as a primary source of excitons is generally called host, while secondary triplet emitter is called guest or dopant.

FIG. 1 shows an organic light-emitting device 100. The figures are not necessarily drawn to scale. Device 100 may include a substrate 110, an anode 115 and 215, a hole injection layer 120, a hole transport layer 125 and 225, an electron blocking layer 130, an emissive layer 135, a hole blocking layer 140, an electron transport layer 145, an electron injection layer 150, a protective layer 155, and a cathode 160 and

240. Cathode 160 and 240 is a compound cathode having a first conductive layer 162 and a second conductive layer 164. Device 100 may be fabricated by depositing the layers described, in order.

Figure 2:
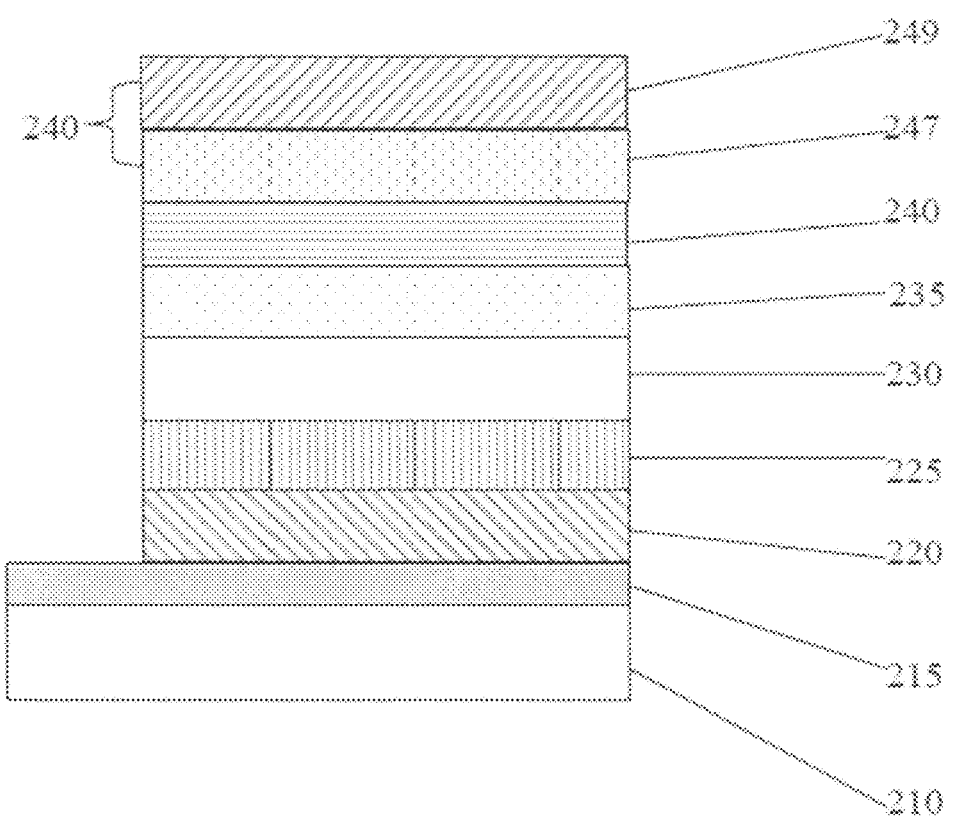
FIG. 2 shows a simplified organic light emitting device having separate emissive, hole transport, and emissive layers, as well as other layers.

FIG. 2 shows a simplified organic light-emitting device 200. The figures are not necessarily drawn to scale. Device 200 may include a substrate 210, an anode 215, a hole injection layer 220, a hole transport layer 225, an emissive layer 230, an electron injection layer 235, a protective layer 240, and a cathode 245. Cathode 245 is a compound cathode having a first conductive layer 247 and a second conductive layer 249. Device 200 may be fabricated by depositing the layers described, in order.

Substrate 110 and 210 may be any suitable substrate that provides desired structural properties. Substrate 110 and 210 may be flexible or rigid. Substrate 110 and 210 may be transparent, translucent or opaque. Plastic and glass are examples of preferred rigid substrate materials. Plastic and metal foils are examples of preferred flexible substrate materials. Substrate 110 and 210 may be a semiconductor material in order to facilitate the fabrication of circuitry. For example, substrate 110 and 210 may be a silicon wafer upon which circuits are fabricated, capable of controlling OLEDs subsequently deposited on the substrate. Other substrates may be used. The material and thickness of substrate 110 and 210 may be chosen to obtain desired structural and optical properties.

Anode 115 and 215 may be any suitable anode that is sufficiently conductive to transport holes to the organic layers. The material of anode 115 and 215 preferably has a work function higher than about 4 eV (a "high work function material"). Preferred anode materials include conductive metal oxides, such as indium tin oxide (ITO) and indium zinc oxide (IZO), cadmium tin oxide (CTO), aluminum zinc oxide (AlZnO), and metals. Anode 115 and 215 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 and 215 may be opaque and/or reflective. A reflective anode 115 and 215 may be preferred for some top-emitting devices, to increase the amount of light emitted from the top of the device. The material and thickness of anode 115 and 215 may be chosen to obtain desired conductive and optical properties. Where anode 115 and 215 is transparent, there may be a range of thickness for a particular material that is thick enough to provide the desired conductivity, yet thin enough to provide the desired degree of transparency. Other anode materials and structures may be used.

Hole transport layer 125 and 225 may include a material capable of transporting holes. Hole transport layer 125 and 225 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in U.S. patent application Ser. No. 10/173,682 to Forrest et al., which is incorporated by reference in its entirety. Other hole transport layers may be used.

Emissive layer 135 and 230 may include an organic material capable of emitting light when a current is passed between anode 115 and 215 and cathode 160 and 240. Emissive layer 135 and 230 may comprise a host material capable of transporting electrons and/or holes, doped with an emissive material that may trap electrons, holes, and/or excitons, such that excitons relax from the emissive material via a photoemissive mechanism. Preferably, emissive layer 135 and 230 contains a phosphorescent guest or dopant, although fluorescent emissive materials may also be used, and a host material. These may include host materials according to the present invention. Combinations of hightriplet hosts and phosphorescent materials are preferred because of the higher luminescent efficiencies associated with such materials. The emissive layer 135 and 230 may comprise other materials, such as dopants that tune the emission of the emissive material. Emissive layer 135 and 230 may include a plurality of emissive materials capable of, in combination, emitting a desired spectrum of light. Examples of host materials include CBP and TPBI. Examples of emissive dopant materials are disclosed in D'Andrade, B; Thompson, M. E.; Forrest, S. R. PCT Int. Appl. 2002, WO 2002091814, which is incorporated by reference in its entirety. Emissive material may be included in emissive layer 135 and 230 in a number of ways. For example, an emissive small molecule may be incorporated into a blend of small-molecule hosts or a polymer. Other emissive layer materials and structures may be used.

Electron transport layer 140 may include a material capable of transporting electrons. Electron transport layer 140 may be intrinsic (undoped), or doped. Doping may be used to enhance conductivity. Alga is an example of an intrinsic electron transport layer. An example of an n-doped electron transport layer is BPhen doped with Li at a molar ratio of 1:1, as disclosed in U.S. patent application Ser. No. 10/173,682 to Forrest et al., which is incorporated by reference in its entirety. Other electron transport layers may be used.

Cathode 160 and 240 may be any suitable material or combination of materials known to the art, such that cathode 160 and 240 is capable of conducting electrons and injecting them into the organic layers of device 100. Cathode 160 and 240 may be transparent or opaque, and may be reflective. Metals and metal oxides are examples of suitable cathode materials. Cathode 160 and 240 may be a single layer, or may have a compound structure. FIG. 1 shows a compound cathode 160 and 240 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 and 240 that is in contact with the underlying organic layer, whether it is a single layer cathode 160 and 240, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron-blocking layer 130 may be disposed between emissive layer 135 and 230 and the hole transport layer 125 and 225, to block electrons from leaving emissive layer 135 and 230 in the direction of hole transport layer 125 and 225. Similarly, a hole blocking layer 140 may be disposed between emissive layer 135 and 230 and electron transport layer 145, to block holes from leaving emissive layer 135 and 230 in the direction of electron transport layer 140. Blocking layers may also be used to block excitons from diffusing out of the emissive layer. The theory and use of blocking layers is described in more detail in U.S. Pat. No.

6,097,147 and U.S. patent application Ser. No. 10/173,682 to Forrest et al., which are incorporated by reference in their entireties.

Generally, injection layers are comprised of a material that may improve the injection of charge carriers from one layer, such as an electrode or an organic layer, into an adjacent organic layer. Injection layers may also perform a charge transport function. In device 100 and 200, hole injection layer 120 and 220 may be any layer that improves the injection of holes from anode 115 and 215 into hole transport layer 125 and 225. CuPc is an example of a material that may be used as a hole-injection layer from an ITO anode 115 and 215, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100 and 200. More examples of injection layers are provided in U.S. Pat. No. 7,061,175 to Weaver et al., which is incorporated by reference in its entirety.

A protective layer may be used to protect underlying layers during subsequent fabrication processes. For example, the processes used to fabricate metal or metal oxide top electrodes may damage organic layers, and a protective layer may be used to reduce or eliminate such damage. In device 100 and 200, protective layer 155 and 240 may reduce damage to underlying organic layers during the fabrication of cathode 160 and 240. Preferably, a protective layer has a high carrier mobility for the type of carrier that it transports (electrons in device 100 and 200), such that it does not significantly increase the operating voltage of device 100 and 200. CuPc, BCP, and various metal phthalocyanines are examples of materials that may be used in protective layers. Other materials or combinations of materials may be used. The thickness of protective layer 155 and 240 is preferably thick enough that there is little or no damage to underlying layers due to fabrication processes that occur after organic protective layer 160 and 240 is deposited, yet not so thick as to significantly increase the operating voltage of device 100 and 200. Protective layer 155 and 240 may be doped to increase its conductivity. For example, a CuPc or BCP protective layer 155 may be doped with Li. A more detailed description of protective layers may be found in U.S. patent application Ser. No. 09/931,948 to Lu et al., which is incorporated by reference in its entirety.

The simple layered structure illustrated in FIG. 1 is provided by way of non-limiting example, and it is understood that embodiments of the invention may be used in connection with a wide variety of other structures included inverted structure or structures where one or more layers may be omitted from the structure of device 100. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting.

Structures and materials not specifically described may also be used, such as OLEDs comprised of polymeric materials (PLEDs) such as disclosed in U.S. Pat. No. 5,247,190, Friend et al., which is incorporated by reference in its entirety. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and organic vapor jet deposition (OVJD), such as described in U.S. patent application Ser. No. 10/233,470, which is incorporated by reference in its entirety. Other suitable deposition methods include spin coating and other solution based processes. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use at various temperatures, preferably within a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as light-emitting transistors, field-effect transistors, organic solar cells and organic photodetectors may employ the materials and structures. More generally, organic devices, such as organic transistors, may employ the materials and structures of this invention.

"Stability" may be measured in a number of ways. One stability measurement is the operational stability of the electroluminescent device. The operational half-life is the time required for the luminance of the device to decay from the initial luminance ($L_0$) to 50% of its initial luminance ($L_{0.5}$) under constant current and at room temperature unless otherwise noted. The devices of the present invention can advantageously have an operational half-life in excess of 5000 hours.

In an embodiment of the present invention, an emissive layer having improved efficiency or charge transport properties or both emissive efficiency and charge transport properties when incorporated into an organic light-emitting device is provided. The emissive layer includes a host material of the following structure (Formula IV):

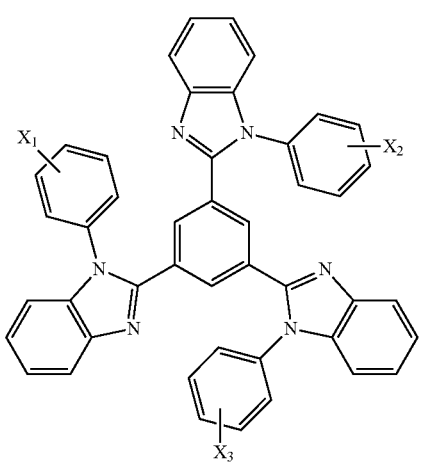

IV wherein $X_1$ is a substituent selected from the group consisting of H, CN, $CO_2R$, C(O)R, $NR_2$, $NAr_2$, OR, SR, SOR, $SO_2R$, $SO_3H$, $SO_2NR_1R_2$, $B(OH)_2$, $B(OR_1)(OR_2)$, halo, alkyl, fluoroalkyl, fluoroalkenyl, fluoroalkynyl, aryl, heteroaryl or heterocyclic group, wherein said alkyl, alkylaryl, alkenyl, alkenylaryl, alkynyl, alkynylaryl, aryl, heteroaryl or heterocyclic group is unsubstituted or optionally, substituted;

$X_2$ is a substituent selected from the group consisting of H, CN, $CO_2R$, C(O)R, $NR_2$, $NAr_2$, OR, SR, SOR, $SO_2R$, $SO_3H$, $SO_2NR_1R_2$, $B(OH)_2$, $B(OR_1)(OR_2)$, halo, alkyl, fluoroalkyl, fluoroalkenyl, fluoroalkynyl, aryl, heteroaryl or heterocyclic group, wherein said alkyl, alkylaryl, alkenyl, alkenylaryl, alkynyl, alkynylaryl, aryl, heteroaryl or heterocyclic group is unsubstituted or optionally, substituted;

$X_3$ is a substituent selected from the group consisting of H, CN, $CO_2R$, C(O)R, $NR_2$, $NAr_2$, OR, SR, SOR, $SO_2R$, $SO_3H$, $SO_2NR_1R_2$, $B(OH)_2$, $B(OR_1)(OR_2)$, halo, alkyl, fluoroalkyl, fluoroalkenyl, fluoroalkynyl, aryl, heteroaryl or heterocyclic group, wherein said alkyl, alkylaryl, alkenyl, alkenylaryl, alkynyl, alkynylaryl, aryl, heteroaryl or heterocyclic group is unsubstituted or optionally, substituted;

The substituents R, $R_1$, $R_2$ and $R_3$ are independently preferably hydrogen, methyl or ethyl.

Although not limited by theory of operation, it is believed that an electron-rich groups such as 9H-carbazole-9-yl or N,N-diphenylamine moiety at the position $X_1$, $X_2$ or $X_3$ of the structure IV advantageously provides improved charge-transporting properties. Specifically, the TPBI moiety transports electrons while the carbazole-9-yl, N,N-diphenylamine, N,N-di(methoxyphenyl)amine or N,N-di(methylphenyl) amine improves hole transport abilities of the material.

The combination of the electron-transport TPBI moiety and the electron-transporting moieties renders the resulting host material capable of transporting both electrons and holes, thus constituting bipolar or ambipolar transport material.

The preferable non-limiting examples of the specific moieties are shown in the Table I:

TABLE I

| $X_1$ | $X_2$ | $X_3$ |
|---|---|---|
| H | H | (carbazole) |
| H | (carbazole) | (carbazole) |
| (carbazole) | (carbazole) | (carbazole) |

TABLE I-continued

| $X_1$ | $X_2$ | $X_3$ |
|---|---|---|
| H | H | 3,6-di-tert-butylcarbazol-9-yl |
| H | 3,6-di-tert-butylcarbazol-9-yl | 3,6-di-tert-butylcarbazol-9-yl |
| 3,6-di-tert-butylcarbazol-9-yl | 3,6-di-tert-butylcarbazol-9-yl | 3,6-di-tert-butylcarbazol-9-yl |
| H | H | diphenylamino |
| H | diphenylamino | diphenylamino |
| diphenylamino | diphenylamino | diphenylamino |
| H | H | di(4-methylphenyl)amino |
| H | di(4-methylphenyl)amino | di(4-methylphenyl)amino |

TABLE I-continued

| X₁ | X₂ | X₃ |
|---|---|---|
| 4-MeC₆H₄–N(–C₆H₄-4-Me)– | 4-MeC₆H₄–N(–C₆H₄-4-Me)– | 4-MeC₆H₄–N(–C₆H₄-4-Me)– |
| H | H | 4-MeOC₆H₄–N(–C₆H₄-4-OMe)– |
| H | 4-MeOC₆H₄–N(–C₆H₄-4-OMe)– | 4-MeOC₆H₄–N(–C₆H₄-4-OMe)– |
| 4-MeOC₆H₄–N(–C₆H₄-4-OMe)– | 4-MeOC₆H₄–N(–C₆H₄-4-OMe)– | 4-MeOC₆H₄–N(–C₆H₄-4-OMe)– |
| H | H | 3,6-bis(carbazol-9-yl)carbazol-9-yl |
| H | 3,6-bis(carbazol-9-yl)carbazol-9-yl | 3,6-bis(carbazol-9-yl)carbazol-9-yl |
| 3,6-bis(carbazol-9-yl)carbazol-9-yl | 3,6-bis(carbazol-9-yl)carbazol-9-yl | 3,6-bis(carbazol-9-yl)carbazol-9-yl |

TABLE I-continued
| $X_1$ | $X_2$ | $X_3$ |
|---|---|---|
| H | H | 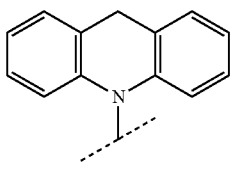 |
| H | 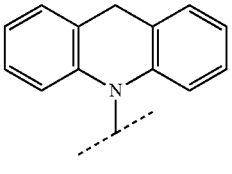 | 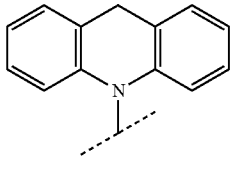 |
| 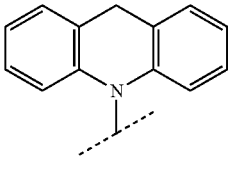 | 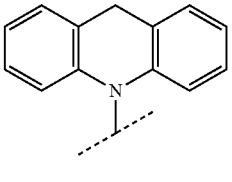 | 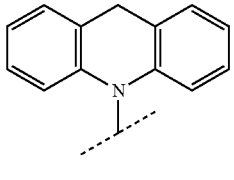 |
| H | H | 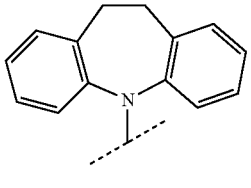 |
| H | 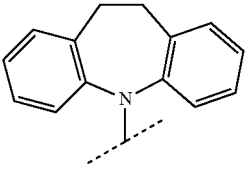 | 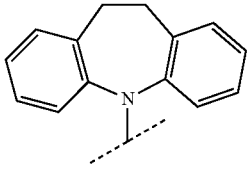 |
| 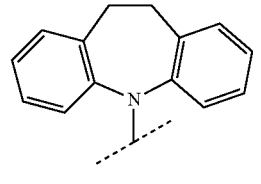 | 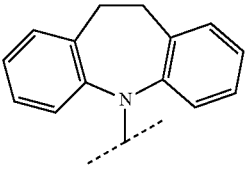 | 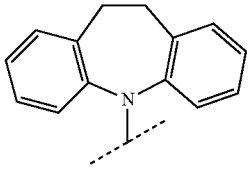 |
| H | H | 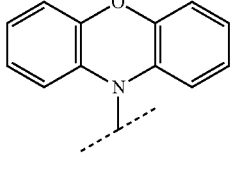 |
| H | 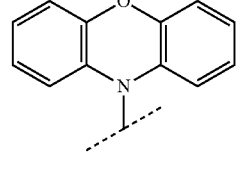 | 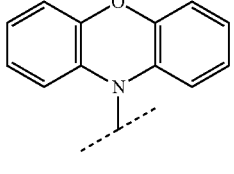 |
| 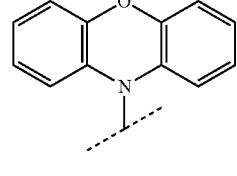 | 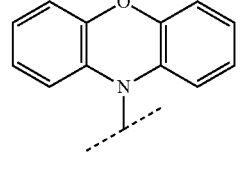 | 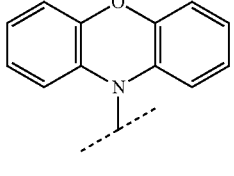 |

TABLE I-continued

| X₁ | X₂ | X₃ |
|---|---|---|
| H | H | phenazine-N(R) |
| H | phenazine-N(R) | phenazine-N(R) |
| phenazine-N(R) | phenazine-N(R) | phenazine-N(R) |
| H | H | phenazine-N(Ar) |
| H | phenazine-N(Ar) | phenazine-N(Ar) |
| phenazine-N(Ar) | phenazine-N(Ar) | phenazine-N(Ar) |
| H | H | phenazine-N(HxAr) |

TABLE I-continued
| $X_1$ | $X_2$ | $X_3$ |
|---|---|---|
| H | HxAr-phenazine 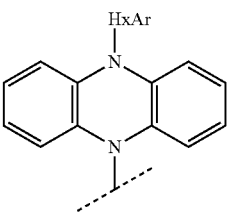 | HxAr-phenazine 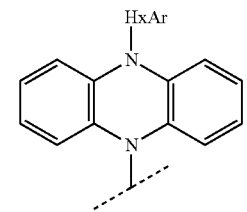 |
| HxAr-phenazine 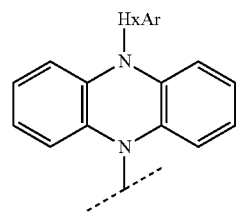 | HetAr-phenazine 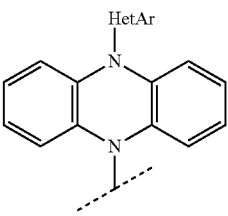 | HetAr-phenazine 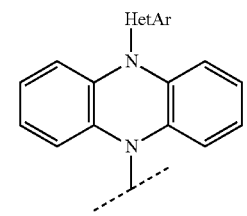 |
| H | H | fluorene 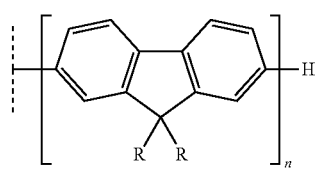 |
| H | fluorene 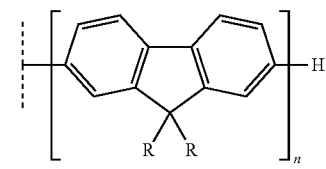 | fluorene 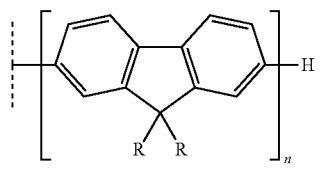 |
| fluorene 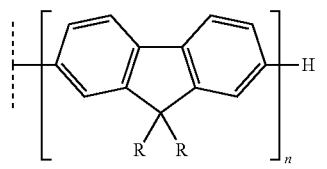 | fluorene 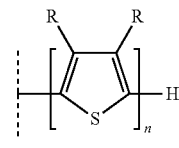 | fluorene 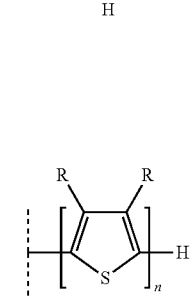 |
| H | H | thiophene 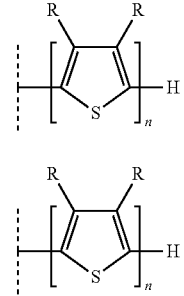 |
| H | thiophene | thiophene |
| thiophene | thiophene | thiophene |
| H | H | pyridine 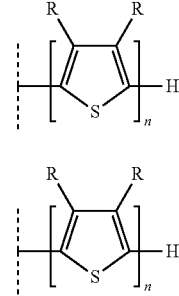 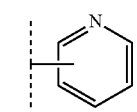 |

TABLE I-continued

| $X_1$ | $X_2$ | $X_3$ |
|---|---|---|
| H | pyridyl | pyridyl |
| pyridyl | pyridyl | pyridyl |

In another embodiment of the present invention, an emissive layer having improved efficiency or charge transport properties or both emissive efficiency and charge transport properties when incorporated into an organic light-emitting device is provided. The emissive layer includes a host material of the following structure (Formula V):

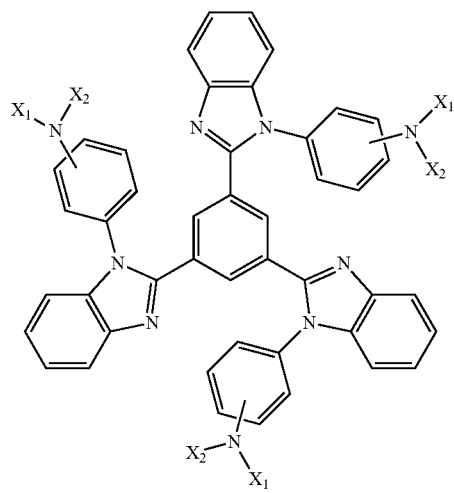

V wherein $X_1$ is a substituent selected from the group consisting of alkyl, aryl, heteroaryl or heterocyclic group, wherein said alkyl, aryl, heteroaryl or heterocyclic group is unsubstituted or optionally, substituted;

$X_2$ is a substituent selected from the group consisting of alkyl, aryl, heteroaryl or heterocyclic group, wherein said alkyl, aryl, heteroaryl or heterocyclic group is unsubstituted or optionally, substituted;

The preferable non-limiting examples of the specific moieties are shown in the Table II:

TABLE II

| $X_1$ | $X_2$ |
|---|---|
| phenyl | phenyl |
| phenyl | phenyl-R |
| phenyl | phenyl-OR |
| phenyl | naphthyl |
| phenyl | thienyl |
| naphthyl | naphthyl |
| naphthyl | thienyl |
| phenyl-R | phenyl-R |
| phenyl-R | phenyl-OR |
| phenyl-R | naphthyl |
| phenyl-R | thienyl |

TABLE II-continued

| X₁ | X₂ |
|---|---|
| ![phenyl-OR] | ![phenyl-OR] |
| ![phenyl-OR] | ![naphthyl] |
| ![phenyl-OR] | ![thiophene-S] |

In yet another embodiment of the present invention, an emissive layer having improved efficiency or charge transport properties or both emissive efficiency and charge transport properties when incorporated into an organic light-emitting device is provided. The emissive layer includes a host material of the following structure (Formula VI):

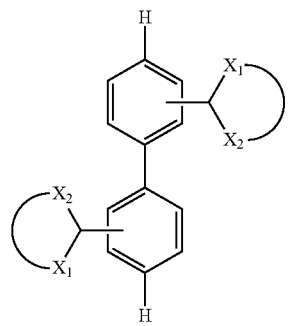

wherein $X_1$ is a substituent selected from the group consisting of alkyl, aryl, heteroaryl or heterocyclic group, wherein said alkyl, aryl, heteroaryl or heterocyclic group is unsubstituted or optionally, substituted;

$X_2$ is a substituent selected from the group consisting of alkyl, aryl, heteroaryl or heterocyclic group, wherein said alkyl, aryl, heteroaryl or heterocyclic group is unsubstituted or optionally, substituted;

$X_1$ and $X_2$ form a cyclic structure or ring;

The preferable non-limiting examples of the specific $-N<X_1/X_2$

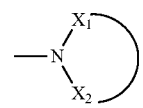

moieties are shown in the Table III:

TABLE III

| where  is | 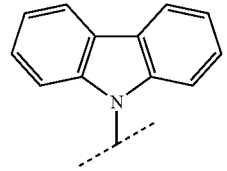 |
|---|---|
| where  is | 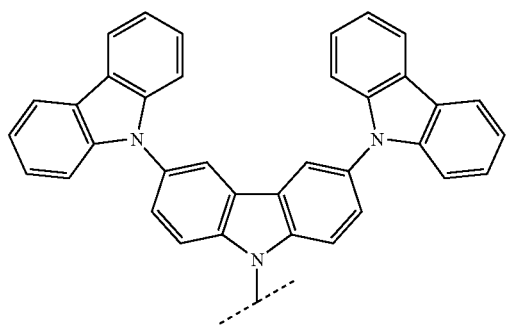 |

TABLE III-continued
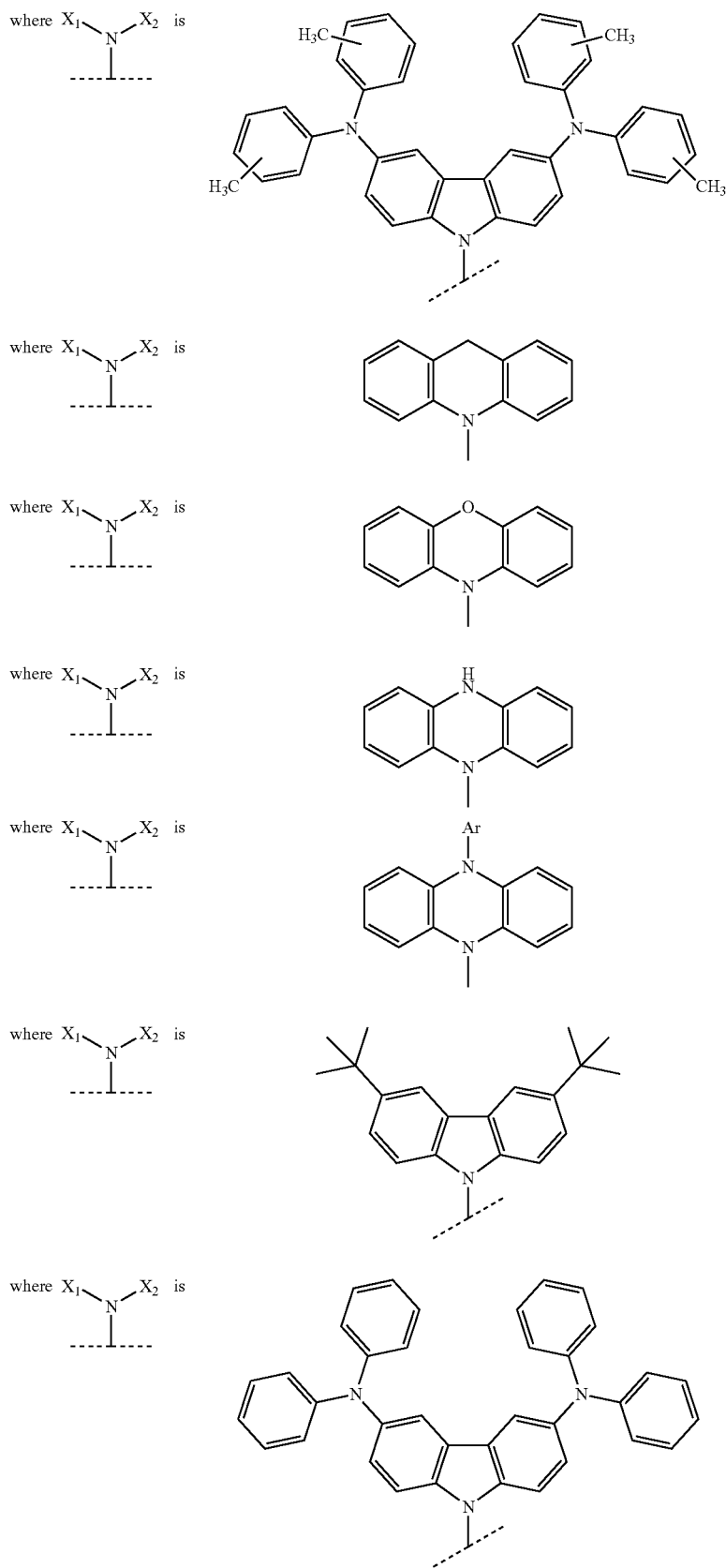

TABLE III-continued where $X_1\text{-}N\text{-}X_2$ is

[structure: 3,6-bis[bis(methoxyphenyl)amino]carbazole with N-substitution point]

where $X_1\text{-}N\text{-}X_2$ is

[structure: 10,11-dihydro-5H-dibenz[b,f]azepine with N-substitution point]

| $X_1$ | $X_2$ |
|---|---|
| phenyl | phenyl |
| phenyl | phenyl-R |
| phenyl | phenyl-OR |
| phenyl | naphthyl |
| phenyl | thienyl |
| naphthyl | naphthyl |
| naphthyl | thienyl |
| phenyl-R | phenyl-R |
| phenyl-R | phenyl-OR |

TABLE III-continued

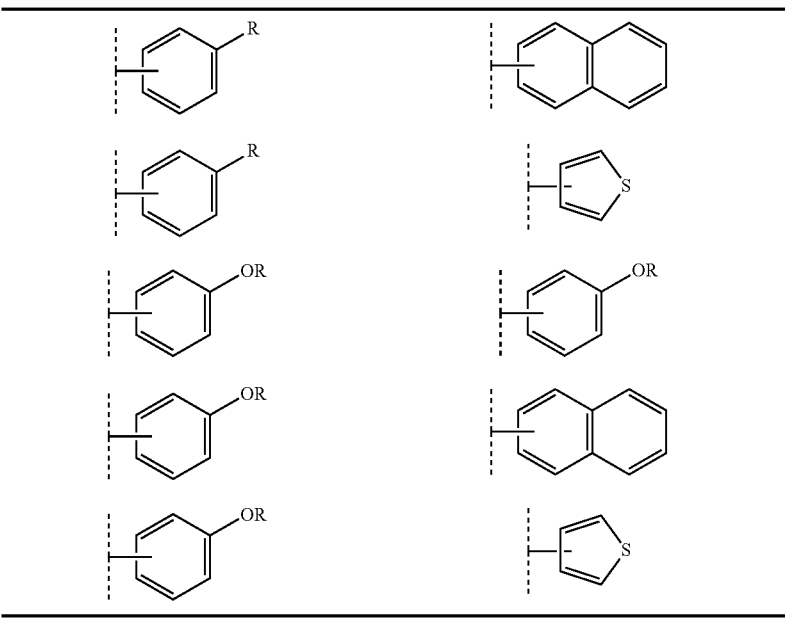

The term "heteroatom" as used herein includes oxygen, nitrogen, sulfur or phosphorus and combinations thereof.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, C(O)R, $NR_2$, cyclic-amino, $NO_2$, and OR.

The term "cycloalkyl" as used herein contemplates cyclic alkyl radicals. Preferred cycloalkyl groups are those containing 3 to 7 carbon atoms and include cyclobutyl, cyclopentyl, cyclohexyl, and the like. Additionally, the cycloalkyl group may be optionally substituted with one or more substituents selected from halo, CN, $CO_2R$, C(O)R, $NR_2$, cyclic-amino, $NO_2$, and OR.

The term "cycloalkenyl" as used herein contemplates cyclic alkyl radicals containing at least one double bond. Preferred cycloalkenyl groups are those containing 3 to 7 carbon atoms and include cyclobutenyl, cyclopentenyl, cyclohexenyl, and the like. Additionally, the cycloalkenyl group may be optionally substituted with one or more substituents selected from halo, CN, $CO_2R$, C(O)R, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, C(O)R, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, C(O)R, $NR_2$, cyclic-amino, $NO_2$, and OR.

The terms "alkylaryl" as used herein contemplates an alkyl group which has as a substituent an aromatic group. Additionally, the alkylaryl group may be optionally substituted on the aryl with one or more substituents selected from halo, CN, $CO_2R$, C(O)R, $NR_2$, cyclic-amino, $NO_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperidino, pyrrolidino, and the like, and cyclic ethers, such as tetrahydrofuran, tetrahydropyran, and the like.

The term "aryl" or "aromatic group" as used herein contemplates single-ring aromatic groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

Material Definitions:

As used herein, abbreviations refer to materials as follows:
BCP: 2,9-dimethyl-4,7-diphenyl-1,10-phenanthroline
BPhen: 4,7-diphenyl-1,10-phenanthroline
n-BPhen: n-doped BPhen (doped with lithium)
CBP: N,N'-dicarbazolyl-4,4'-biphenyl
mCP: 1,3-dicarbazole-benzene
CuPc: copper phthalocyanine
DCM: 4-(dicyanomethylene)-6-(4-dimethylaminostyryl-2-methyl)-4H-pyran
DMQA: N,N'-dimethylquinacridone FIrpic: iridium(III)bis[(4,6-difluorophenyl)-pyridinato-N, C2]picolinate
F$_4$-TCNO: tetrafluoro-tetracyano-quinodimethane
Ir(ppy)$_3$: tris(2-phenylpyridine)-iridium
Ir(ppz) 3: tris(1-phenylpyrazoloto,N,C(2')iridium(III)
Ir(ppy)$_2$acac: bis(2-phenylpyridine)acetylacetonatoiridium (III)
ITO: indium tin oxide
α-NPD: 4,4'-bis[N-(1-naphtyl)-N-phenylamino]biphenyl
p-MTDATA: p-doped m-MTDATA (doped with F$_4$-TCNQ)
PEDOT-PSS: poly(ethylenedioxy-thiophene) doped with poly(p-styrenesulfonic acid)
TAZ: 3-phenyl-4-(1'-naphthyl)-5-phenyl-1,2,4-triazole
TPBI: 1,3,5-tris(phenyl-2-benzimidazolyl)benzene
TPD: N,N'-bis(3-methylphenyl)-N,N'-bis-(phenyl)-benzidine
TCO: transparent conductive oxide

EXAMPLES

Specific representative embodiments of the invention will now be described, including how such embodiments may be made. It is understood that the specific methods, materials, conditions, process parameters, apparatus and the like do not necessarily limit the scope of the invention.

Example 1

Synthesis of 1,3,5-tris[1-(4-bromophenyl)-1H-benzo[d]imidazol-2-yl]benzene (Compound 1)

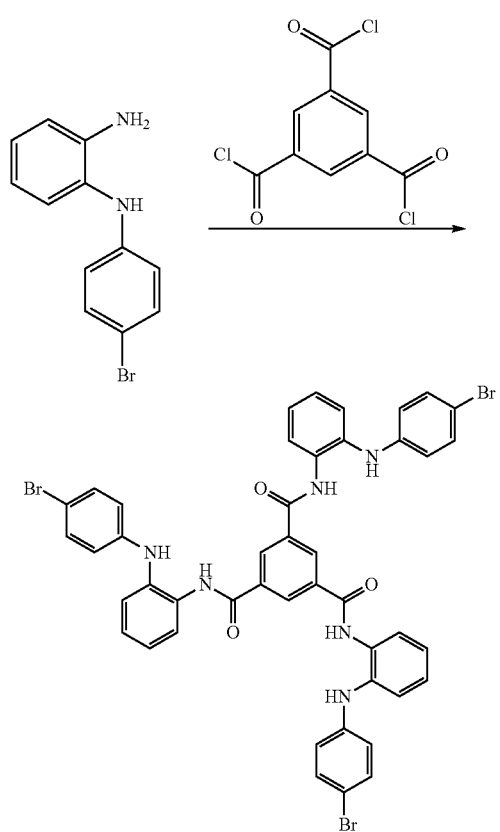

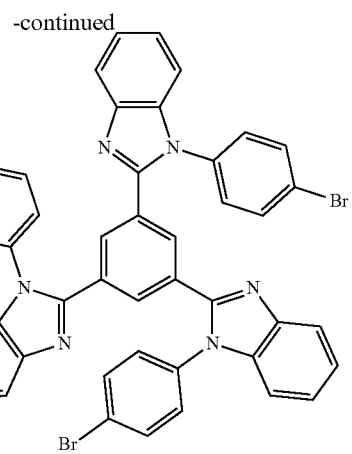

N-(4-bromophenyl)-1,2-phenylenediamine (1.64 g, 6.23 mmol) was dissolved in 1-methyl-2-pyrrolidinone (NMP) (7 mL). To the solution 1,3,5-benzenetricarbonyl trichloride (0.551 g, 2.08 mmol) was added portion-wise under nitrogen. The reaction mixture was stirred at room temperature for 2 h, and then the reaction temperature was raised to 50° C. for additional 30 min. After cooling the reaction mixture was poured into cold water (50 mL). The resulting precipitates were filtered off and washed with water to give crude tribenzamide. The tribenzamide was heated at 250° C. for 3 h under nitrogen. After cooling water (50 mL) was added to the mixture, and extracted with CH$_2$Cl$_2$ (50×3 mL). The combined organic layers were washed with water and brine, and then dried over Na$_2$SO$_4$. Solvent of the filtrate was removed in vacuo to obtain a crude solid. 1,3,5-Tris[1-(4-bromophenyl)-1Hbenzo[d]imidazol-2-yl]benzene was isolated by silica gel column chromatography (solvent: EtOAc) (1.63 g, 88%). $_1$H NMR (300 MHz, CDCl$_3$, δ): 7.87 (s, 3H), 7.85 (d, J=7.5 Hz, 3H), 7.60 (d, J=8.7 Hz, 6H), 7.27-7.39 (m, 6H), 7.18 (d, J=7.4 Hz, 3H), 7.06 (d, J=8.7 Hz, 6H); $_{13}$C APT NMR (75.5 MHz, CDCl$_3$, δ): 150.6 (C), 143.2 (C), 137.3 (C), 135.8 (C), 133.6 (CH), 131.3 (CH), 131.1 (C), 129.1 (CH), 124.3 (CH), 123.8 (CH), 123.0 (C), 120.6 (CH), 110.6 (CH); MALDI-TOF-MS (m/z): 893 [M+H$_+$]; Anal. calcd for C$_{45}$H$_{27}$Br$_3$N6: C, 60.63; H, 3.05; N, 9.43. Found: C, 60.71; H, 2.93; N, 9.47.

Example 2

Synthesis of 4,4',4''-[2,2',2''-(benzene-1,3,5-triyl)-tris(1H-benzo[d]imidazole-2,1-diyl)]-tris(N,Ndiphenylaniline) (Compound 2)

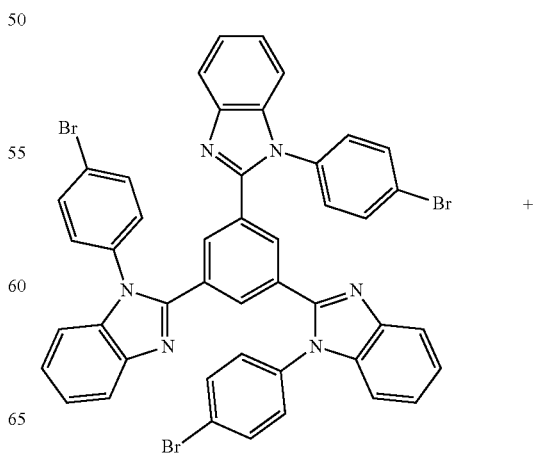

+

-continued

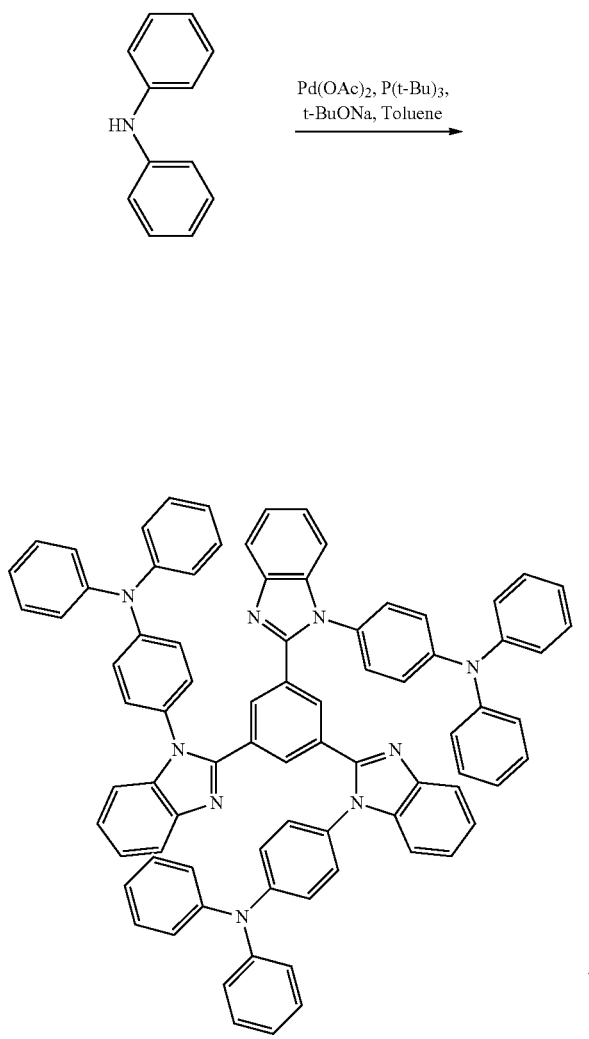

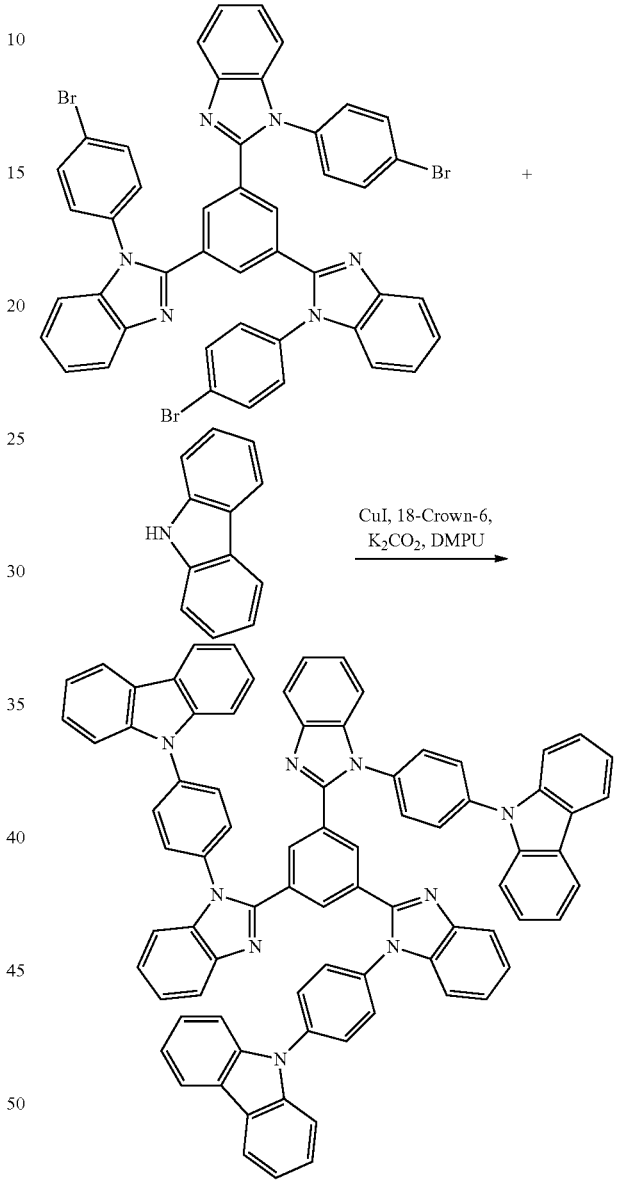

Example 3

Synthesis of 1,3,5-tris(1-(4-(9H-carbazol-9-yl)phenyl)-1H-benzo[d]imidazol-2-yl)benzene (Compound 3)

A mixture of 1,3,5-tris[N-(4-bromophenyl)benzimidazol-2-yl]benzene (0.500 g, 0.560 mmol), diphenylamine (0.570 g, 3.36 mmol), Pd(OAc)$_2$ (0.220 mmol), P(t-Bu)$_3$ (0.900 mmol), NaOtBu (0.480 g, 4.99 mmol) in toluene (5 mL) was refluxed at 110° C. for 70 h under nitrogen. To the reaction mixture water (50 mL) was added, and extracted with CH$_2$Cl$_2$ (50×3 mL). The combined CH$_2$Cl$_2$ layers were washed with water, and dried over Na$_2$SO$_4$. The solution was filtered and the solvent was removed in vacuo. The residue was subjected to column chromatography on silica gel (solvent: EtOAc/CH$_2$Cl$_2$=1/2 followed by 1/1) to afford Compound 2 (0.598 g, 92%). 1H NMR (300 MHz, CDCl$_3$, δ): 7.89-7.91 (m, 6H), 7.33-7.42 (m, 9H), 6.87-7.00 (m, 42H); $_{13}$C APT NMR (75.5 MHz, CDCl$_3$, δ): 151.2 (C), 148.6 (C), 147.2 (C), 143.2 (C), 137.3 (C), 131.3 (CH), 130.7 (C), 129.9 (C), 129.5 (CH), 128.3 (CH), 124.9 (CH), 124.8 (CH), 123.8 (CH), 123.7 (CH), 123.2 (CH), 120.4 (CH), 110.8 (CH); MALDI-TOF-MS (m/z): 1156 [M+H$_+$]; Anal. calcd for C$_{81}$H$_{57}$N9: C, 84.13; H, 4.97; N, 10.90. Found: C, 83.45; H, 5.20; N, 10.53.

A mixture of 1,3,5-tris[N-(4-bromophenyl)benzimidazol-2-yl]benzene (0.800 g, 0.897 mmol), carbazole (0.900 g, 5.38 mmol), CuI (0.049 g, 0.256 mmol), 18-crown-6 (0.093 g, 0.352 mmol) and K$_2$CO$_3$ (1.10 g, 7.99 mmol) was heated in 1,3-dimethyl-3,4,5,6-tetrahydro-2(1H)-pyrimidinone (DMPU) (2 mL) at 210° C. for 64 h under nitrogen. After cooling, 1 N HCl (60 mL) was added to the reaction mixture and extracted with CH$_2$Cl$_2$ (100×3 mL). The combined organic layers were washed with 15% NH$_4$OH (100 mL), water (100 mL), and brine (100 mL). Then, the solution was dried over Na$_2$SO$_4$, and filtration, followed by evaporation of solvent in vacuo, gave a brown oil. Compound 3 was isolated by silica gel column chromatography (solvent: EtOAc/

CH$_2$Cl$_2$=1/2) (0.490 g, 44%). $^1$H NMR (300 MHz, CDCl$_3$, δ): 8.13 (s, 3H), 8.06 (d, J=7.8 Hz, 6H), 7.91 (d, J=7.8 Hz, 3H), 7.60 (d, J=8.7 Hz, 6H), 7.36-7.46 (m, 15H), 7.17 (t, J=7.4 Hz, 6H), 7.07 (d, J=8.1 Hz, 6H), 6.84-6.98 (m, 6H); $_{13}$C APT NMR (75.5 MHz, CDCl$_3$, δ): 150.5 (C), 143.3 (C), 140.7 (C), 138.3 (C), 137.1 (C), 135.5 (C), 131.4 (CH), 130.9 (C), 129.1 (CH), 129.0 (CH), 126.3 (CH), 124.3 (CH), 123.7 (CH), 123.6 (C), 120.8 (CH), 120.5 (CH), 120.5 (CH), 110.7 (CH), 109.3 (CH); MALDI-TOF-MS (m/z): 1150 [M+H$_+$].

Example 4

Synthesis of 1,3,5-tris{1-[4-(trifluoromethyl)phenyl]-1H-benzo[d]imidazol-2-yl}benzene (Compound 4)

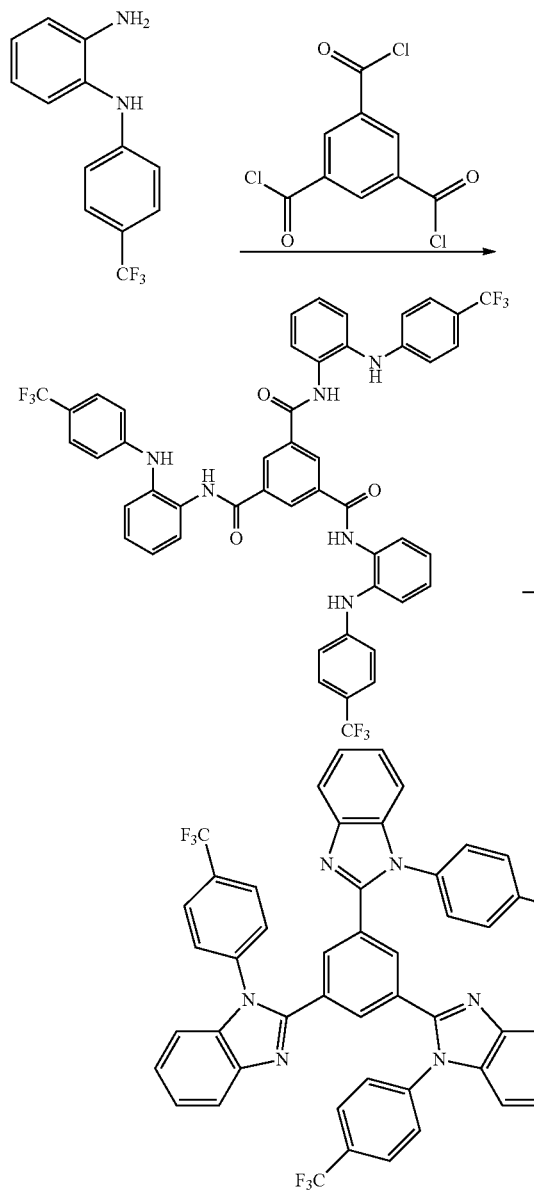

N-(4-Trifluoromethylphenyl)-1,2-phenylenediamine (2.00 g, 7.93 mmol) was dissolved in 1-ethyl-2-pyrrolidinone (NMP) (9 mL). To the solution 1,3,5-benzenetricarbonyl trichloride (0.701 g, 2.64 mmol) was added portionwise under nitrogen. The reaction mixture was stirred at room temperature for 2 h, and then the reaction temperature was raised to 50° C. for additional 30 min. After cooling the reaction mixture was poured into cold water (100 mL). The resulting precipitates were filtered off and washed with water to give crude tribenzamide. The tribenzamide was heated at 250° C. for 3 h under nitrogen. After cooling water (750 mL) was added to the mixture, and extracted with CH$_2$Cl$_2$ (100×3 mL). The combined organic layers were washed with water and brine, and then dried over Na$_2$SO$_4$. Solvent of the filtrate was removed in vacuo to obtain a crude solid. 1,3,5-Tris{1-[4-(trifluoromethyl)phenyl]-1H-benzo[d]imidazol-2-yl}benzene was isolated by silica gel column chromatography (solvent: EtOAc) (1.33 g, 59%). $_1$H NMR (300 MHz, CDCl$_3$, δ): 7.85 (s, 3H), 7.82 (d, J=7.5 Hz, 3H), 7.77 (d, J=8.4 Hz, 6H), 7.28-7.40 (m, 12H), 7.18 (d, J=7.5 Hz, 3H); MALDI-TOFMS (m/z): 859 [M+H$_+$]; Anal. calcd for C$_{48}$H$_{27}$F$_9$N$_6$: C, 67.13; H, 3.17; N, 9.79. Found: C, 67.44; H, 3.03; N, 9.86.

Example 5

Synthesis of 1,3,5-tris[1-(4-t-butylphenyl)-1H-benzo[d]imidazol-2-yl]benzene (Compound 5)

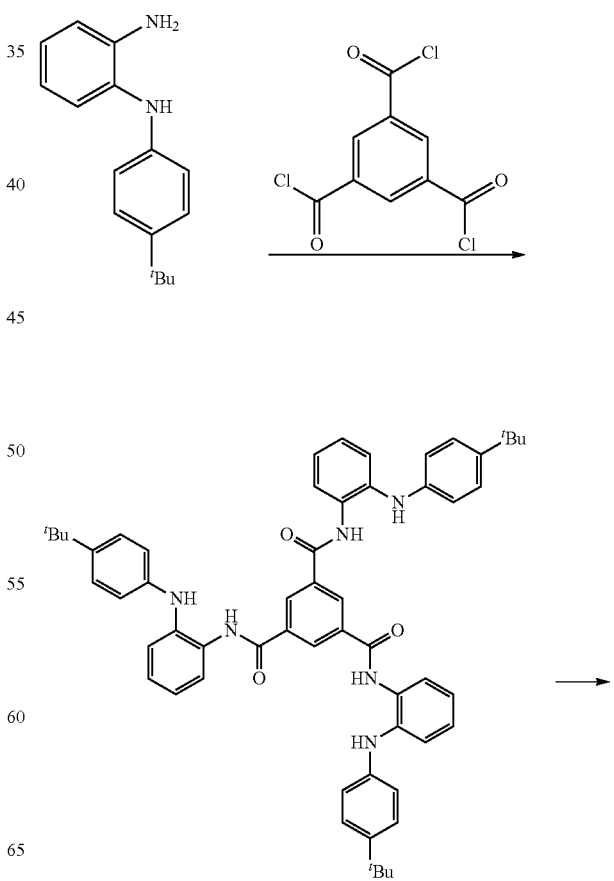

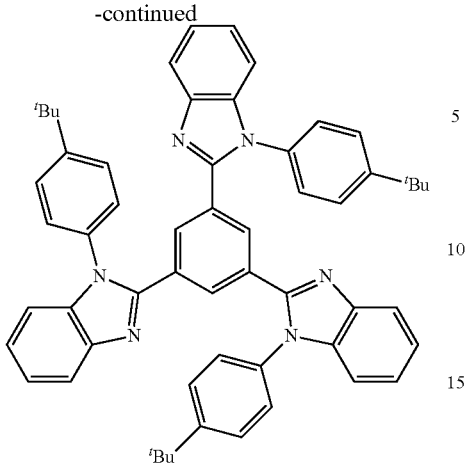

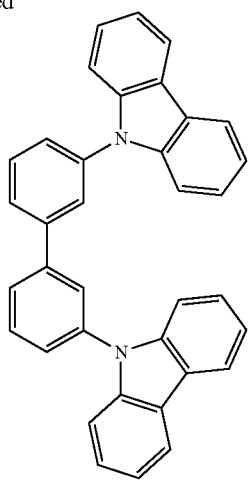

N-(4-t-butylphenyl)-1,2-phenylenediamine (0.461 g, 1.92 mmol) was dissolved in 1-methyl-2-pyrrolidinone (NMP) (2.2 mL). To the solution 1,3,5-benzenetricarbonyl trichloride (0.170 g, 0.639 mmol) was added portionwise under nitrogen. The reaction mixture was stirred at room temperature for 2 h, and then the reaction temperature was raised to 50° C. for additional 30 min. After cooling the reaction mixture was poured into cold water (30 mL). The resulting precipitates were filtered off and washed with water to give crude tribenzamide. The tribenzamide was heated at 250° C. for 3 h under nitrogen. After cooling water (40 mL) was added to the mixture, and extracted with $CH_2Cl_2$ (40×3 mL). The combined organic layers were washed with water and brine, and then dried over $Na_2SO_4$. Solvent of the filtrate was removed in vacuo to obtain a crude solid. 1,3,5-Tris[1-(4-t-butylphenyl)-1Hbenzo[d]imidazol-2-yl]benzene was isolated by silica gel column chromatography (solvent: EtOAc) (0.368 g, 70%). $_1$H NMR (300 MHz, $CDCl_3$, δ): 7.79 (d, J=7.8 Hz, 3H), 7.71 (s, 3H), 7.41 (d, J=8.7 Hz, 6H), 7.18-7.33 (m, 9H), 7.03 (d, J=8.7 Hz, 6H), 1.21 (s, 27H); $_{13}$C APT NMR (75.5 MHz, $CDCl_3$, δ): 152.1 (C), 151.1 (C), 143.0 (C), 137.2 (C), 133.8 (C), 131.3 (C), 130.8 (C), 127.0 (CH), 126.8 (CH), 123.5 (CH), 123.0 (CH), 120.1 (CH), 110.6 (CH), 34.8 (C), 31.3 ($CH_3$); MALDI-TOF-MS (m/z): 823 [M+H$_+$]; Anal. calcd for $C_{57}H_{54}N_6$: C, 83.18; H, 6.61; N, 10.21. Found: C, 83.44; H, 6.70; N, 10.33.

Example 6

Synthesis of N,N'-dicarbazolyl-3,3'-biphenyl (Compound 6)

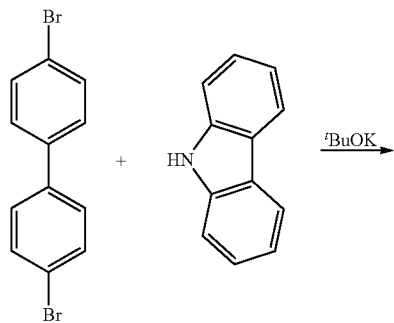

Carbazole (1.80 g, 10.9 mmol), 4,4'-dibromobiphenyl (0.75 g, 2.4 mmol), and potassium tbutoxide (2.24 g, 20 mmol) were dissolved in dry toluene and heated at 135° C. for 24 h. The solution was filtered and the solvent was removed in vacuo, the residue was chromatographed on $SiO_2$ using 10% acetone in hexanes to afford (0.1 g, 8.5%) of the product. $_1$H NMR δ 8.19 (d, J=7.5 Hz, 4H), 7.91-7.60 (m, 8H), 7.55-7.39 (m, 8H), 7.33-7.26 (m, 12H (4H+$CDCl_3$)). $_{13}$C NMR δ 142.8, 140.9, 134.5, 130.3, 126.7, 126.3, 126.0, 125.7, 123.4, 120.3, 120.0, 109.8. EI MS m/z 484 [M$_+$], m.p.>250° C.

Example 7

Alternative synthesis of N,N'-dicarbazolyl-3,3'-biphenyl (Compound 6)

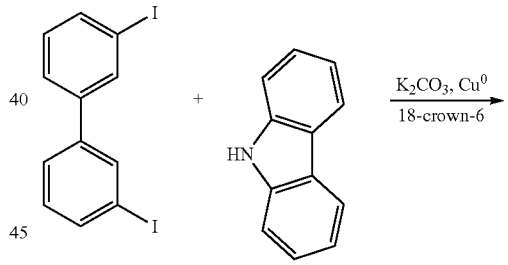

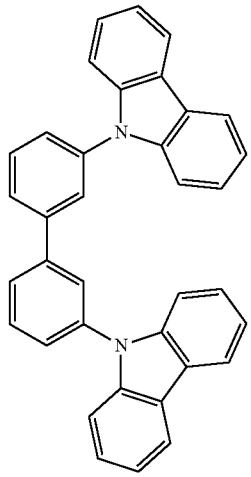

Carbazole (0.90 g, 5.42 mmol), 3,3'-diiodobiphenyl, $K_2CO_3$ (2.72 g, 19.7 mmol), copper powder (0.43 g, 6.77 mmol), and 18-crown-6 (0.13 g, 0.49 mmol) in o-dichlorobenzene were heated to reflux for 48 h. The solution was filtered and the solvent was removed in vacuo, the residue was recrystallized from MeOH to afford the product (0.50 g, 42.5%). $_1$H NMR δ 8.19 (d, J=7.5 Hz, 4H), 7.91-7.60 (m, 8H), 7.55-7.39 (m, 8H), 7.33-7.26 (m, 12H (4H+CDCl$_3$)). $_{13}$C NMR δ 142.8, 140.9, 134.5, 130.3, 126.7, 126.3, 126.0, 125.7, 123.4, 120.3, 120.0, 109.8. EI MS m/z 484 [M$_+$], m.p.>250° C.

Example 8

Synthesis of 9,9'-(biphenyl-3,4'-diyl)bis(9H-carbazole) (Compound 7)

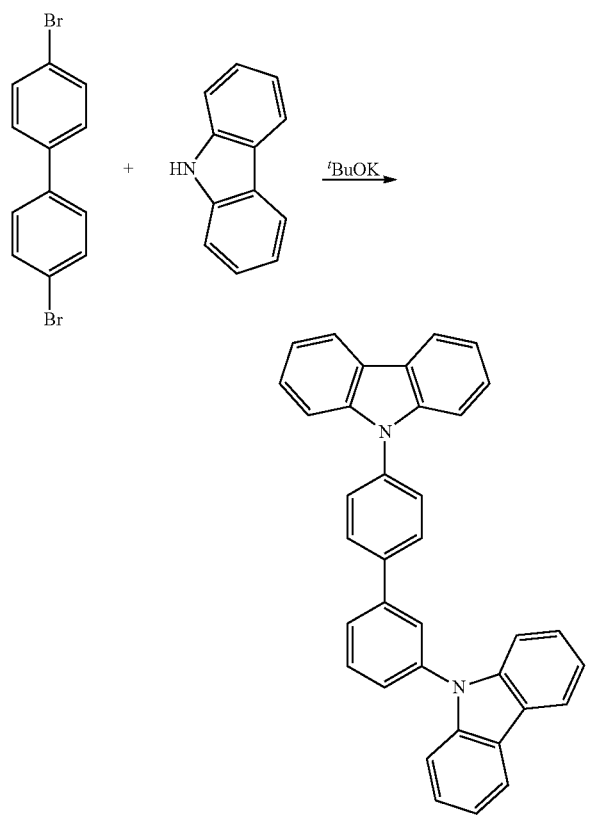 [SMILES: "tBuOK" ; Brc1ccc(-c2ccc(Br)cc2)cc1 ; c1ccc2c(c1)[nH]c1ccccc12 ; c1cc(-c2ccc(-n3c4ccccc4c4ccccc43)cc2)cc(-n2c3ccccc3c3ccccc32)c1]

Carbazole (1.80 g, 10.9 mmol), 4,4'-dibromobiphenyl (0.75 g, 2.4 mmol), and potassium tbutoxide (2.24 g, 20 mmol) were dissolved in dry toluene and heated at 135° C. for 24 h. The solution was filtered and the solvent was removed in vacuo, the residue was dry-packed on SiO$_2$ and chromatographed using 10% acetone in hexanes to afford (0.08 g, 6%) of the product. $_1$H NMR (CDCl$_3$) δ 8.22-8.16 (m, 4H), 7.93-7.65 (m, 8H), 7.56-7.49 (m, 8H), 7.47-7.28 (m, 4H). $_{13}$C NMR (CDCl$_3$+DMSO-d$_6$) δ 142.1, 140.8, 140.7, 139.0, 138.3, 137.3, 130.5, 128.5, 127.3, 126.1, 126.0, 125.9, 125.6, 123.4, 120.3, 120.2, 120.0, 109.7. EI MS m/z 484 [M$_+$], m.p.=244-246° C.

Example 9

Alternative synthesis of 9,9'-(biphenyl-3,4'-diyl)bis(9H-carbazole) (Compound 7)

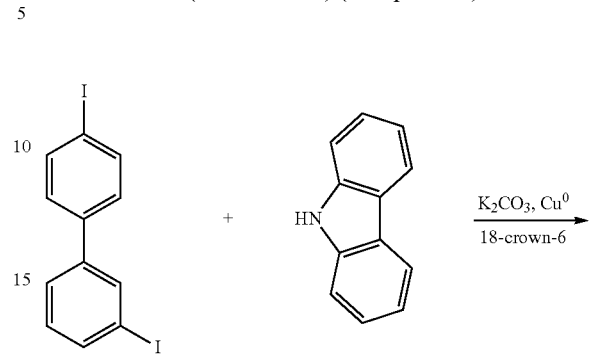

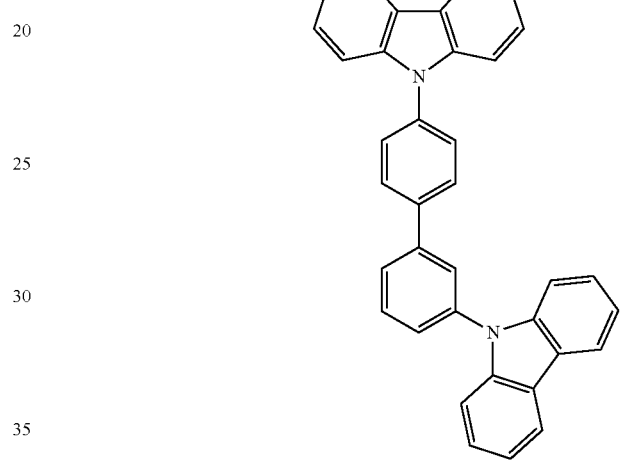

Carbazole (0.90 g, 5.42 mmol), 3,4'-diiodobiphenyl, K$_2$CO$_3$ (2.72 g, 19.7 mmol), copper powder (0.43 g, 6.77 mmol), and 18-crown-6 (0.13 g, 0.49 mmol) were dissolved in o-dichlorobenzene and heated to reflux for 48 h. The solution was filtered and the solvent removed in vacuo, the residue was recrystallized from MeOH to afford the product (0.83 g, 69.7%). $_1$H NMR (CDCl$_3$) δ 8.22-8.16 (m, 4H), 7.93-7.65 (m, 8H), 7.56-7.49 (m, 8H), 7.47-7.28 (m, 4H). $_{13}$C NMR (CDCl$_3$+DMSO-d$_6$) δ 142.1, 140.8, 140.7, 139.0, 138.3, 137.3, 130.5, 128.5, 127.3, 126.1, 126.0, 125.9, 125.6, 123.4, 120.3, 120.2, 120.0, 109.7. EI MS m/z 484 [M$_+$], m.p.=244-246° C.

Example 10

Fabrication of Experimental Device 1

The starting substrates were glass substrates coated with ITO of 200 nm thickness and sheet resistance 10-20 Ω/square, purchased from Delta Technologies, Ltd., Stillwater, Minn. The substrates were degreased with solvents and cleaned with oxygen plasma and UV ozone treatments. All subsequent thin films were deposited by thermal evaporation at a pressure of $10^{-7}$ Torr First CuPc was deposited as a hole injection layer on the anode to a thickness of 10 nm at a rate of 0.3 Å/s. Next, α-NPD was deposited as a hole transport layer at a rate of 1.5 Å/s. Next, an emissive layer comprising a host doped with an appropriate dopant were deposited to form a light emitting layer of desired thickness at a rate of 1.0 Å/s. On top of the light emitting layer, a hole-blocking layer of BCP was deposited at rate 1.5 Å/s. Next, on the electron transport layer, lithium fluoride (LiF) was deposited as an electron injecting layer at a thickness of 0.5 nm at a rate of 0.5 Å/s. Lastly, aluminum (Al) cathode was deposited on the electron injecting layer at a thickness of 100 nm at a rate of 2 Å/s to complete the organic light emitting device.

Fabrication of Experimental Device 2

OLEDs were fabricated on glass-coated ITO substrates from Colorado Concept Coatings (150-200 nm-thick, R☐~20Ω/☐). The ITO-coated substrates, which served as the anode, were degreased by detergent and organic solvents and then UV-ozone cleaned to increase the ITO work function. Poly(3,4-ethylenedioxythiophene) (PEDOT):poly(styrene-4-sulfonate) (PSS) from H.C. Starck (Baytron® P VP Al 4083) was spin-coated over 1 1" ITO substrates at 3000 rpm and baked at 150° C. for 5 minutes to provide a 50 nm film. Next, α-NPD was deposited as a hole transport layer at a rate of 1.5 Å/s. Next, an emissive layer comprising a host doped with an appropriate dopant were deposited to form a light emitting layer of desired thickness at a rate of 1.0 Å/s. On top of the light emitting layer, a hole-blocking layer of BCP was deposited at rate 1.5 Å/s. Organic layers were deposited at ~0.1 nm/sec in a high-vacuum chamber ($10^{-7}$ torr). The electron injection buffer layer CsF (1 nm) and aluminum cathode (100 nm) were also deposited by thermal evaporation at ~0.02 nm/sec and 0.2 nm/sec through a shadow mask.

The devices were characterized by measuring current-voltage and luminance characteristics, as well as spectral output characteristics. All electrical and optical characterization of the diodes was performed using a C9920-12 External Quantum Efficiency Measurement System from Hamamatsu Photonics using a Keithley 2400 as the sourcemeter. Characterization of the devices was performed inside a nitrogen-filled glove-box. The external quantum efficiency was determined as a function of current density.

Phosphorescence emission spectra were recorded using a single-photon-counting spectrofluorometer from Edinburgh Analytical Instruments (FLSP 920) equipped with a pulsed xenon flash-lamp (μF920H, 200-900 nm, 10-100 Hz) for time-gated experiments. For phosphorescence studies at 77 K, the samples were dissolved in spectroscopic grade 2-methyltetrahydrofuran with optical densities around 0.1 at the wavelength of excitation. The samples were placed in quartz EPR tubes (Norrell) and immersed in a Dewar with liquid nitrogen. The signal acquisition of the photomultiplier tube was electronically gated to avoid saturation of the detector by fluorescence.

Figure 3:
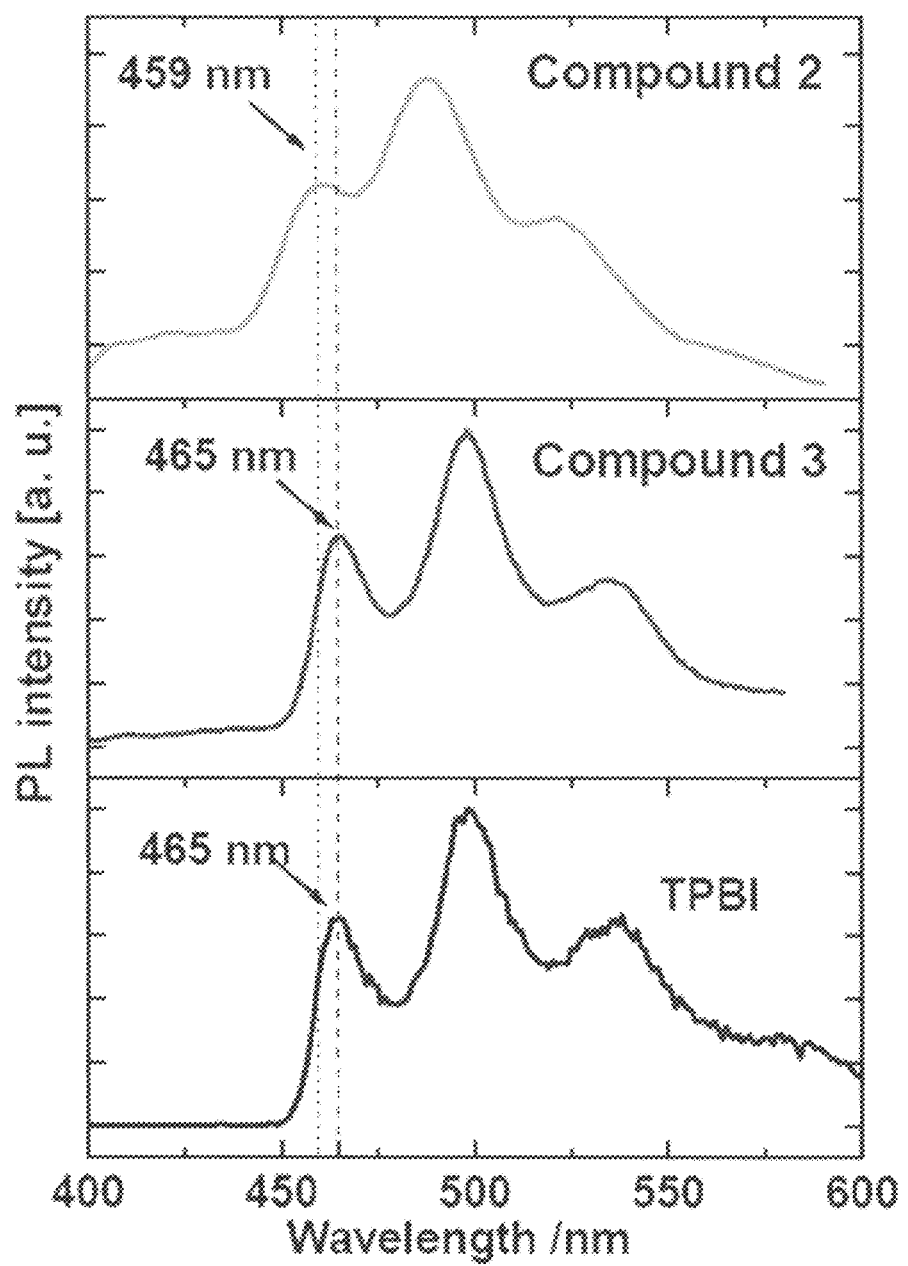
FIG. 3 shows the triplet spectra of TPBI, Compound 2, and Compound 3. The triplet energy of Compound 2 and Compound 3 were found to be 2.70 eV and 2.67 eV, respectively. This is same or higher than the triplet energy of the host TPBI (2.67 eV) and higher than that triplet energy of the dopant FIrpic (2.65 eV).

FIG. 3 shows the triplet spectra of TPBI, Compound 2, and Compound 3. The triplet energy of Compound 2 and Compound 3 were found to be 2.70 eV and 2.67 eV, respectively. This is same or higher than the triplet energy of the host TPBI (2.67 eV). Compound 2 and Compound 3 posses the diphenylamine and carbazole moieties that improve charge transport in the emissive layer thus decreasing the turn-on voltage and improved external quantum efficiency in the corresponding devices.

Figure 4:
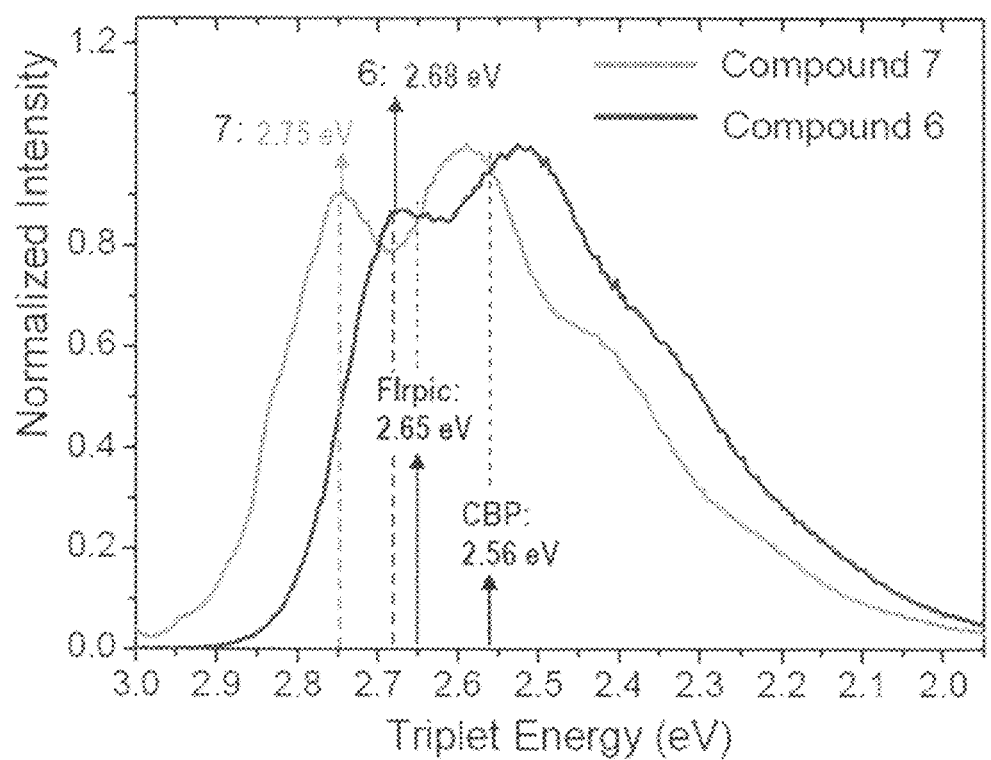
FIG. 4 shows the triplet spectra of CBP, Compound 6, and Compound 7. The triplet energy of Compound 6 and Compound 7 were found to be 2.68 eV and 2.75 eV, respectively. This is significantly higher than the triplet energy of the host CBP (2.56 eV) or dopant FIrpic (2.65 eV).

FIG. 4 shows the triplet spectra of CBP, Compound 6, and Compound 7. The triplet energy of Compound 6 and Compound 7 were found to be 2.68 eV and 2.75 eV, respectively. This is significantly higher than the triplet energy of the host CBP (2.56 eV) or dopant FIrpic (2.65 eV). The high triplet energy of the host prevents the triplet energy transfer from the dopant to the non-emissive host thus contributing to the improved electroluminescence.

Figure 5:
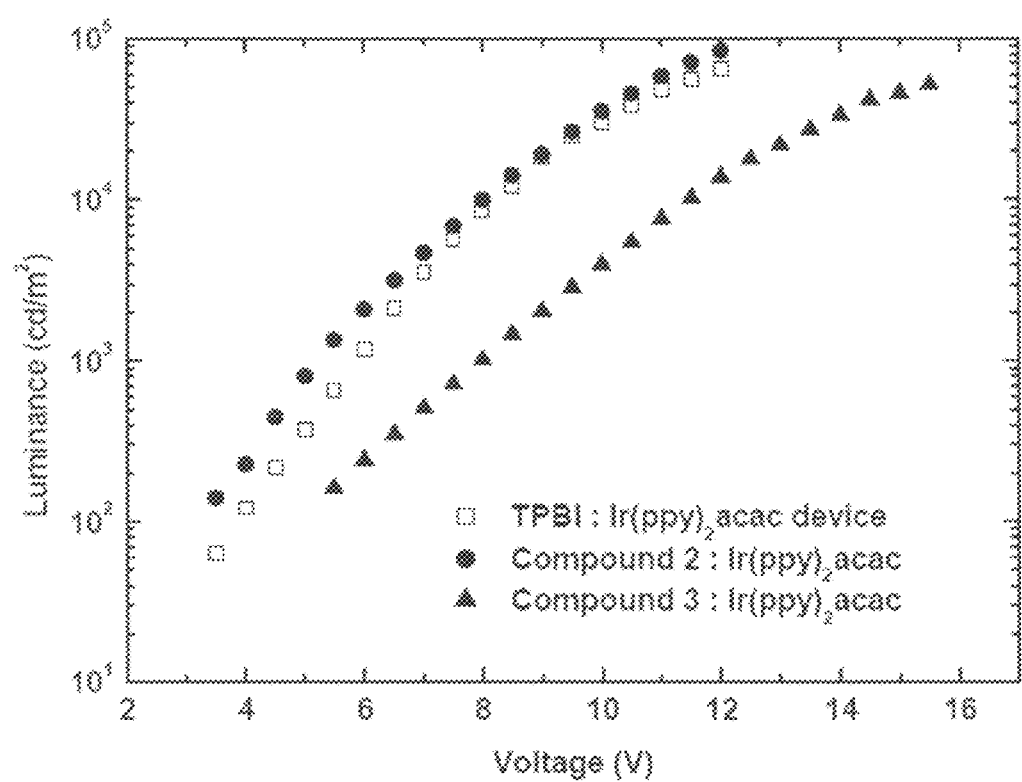
FIG. 5 shows the luminance vs. bias voltage graph for OLEDS comprising an emissive layer composed of Ir(ppy)$_2$acac dopant in TPBI, Compound 2, or Compound 3, respectively.
Figure 6:
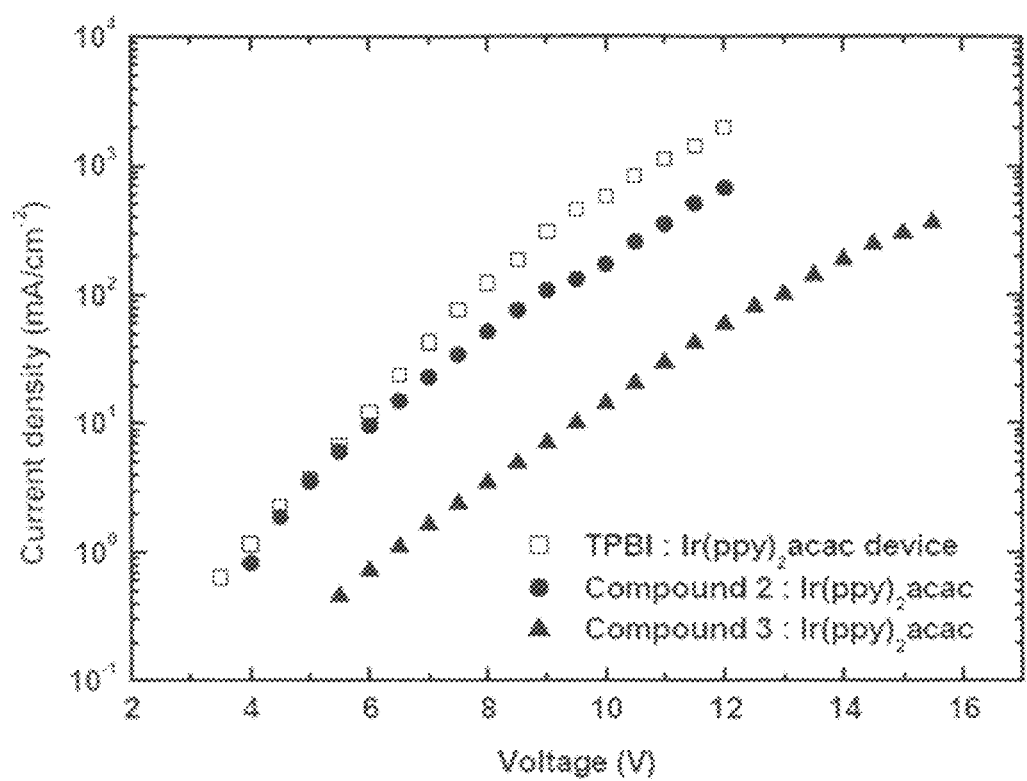
FIG. 6 shows the current density vs. bias voltage graph for OLEDS comprising an emissive layer composed of Ir(ppy)$_2$acac dopant in TPBI, Compound 2, or Compound 3, respectively.

FIG. 5 shows the luminance vs. bias voltage graph for OLEDS comprising an emissive layer composed of Ir(ppy)$_2$acac dopant in TPBI, Compound 2, and Compound 3, respectively. The improved charge transport in device based on Compound 2 shows lower turn-on voltage of 2.5 V while and luminance of 1,000 cd/m$_2$ at voltage of 5.1 V. The TPBI device yields the luminance of 1,000 cd/m$_2$ at voltage of 6.0 V.

Figure 7:
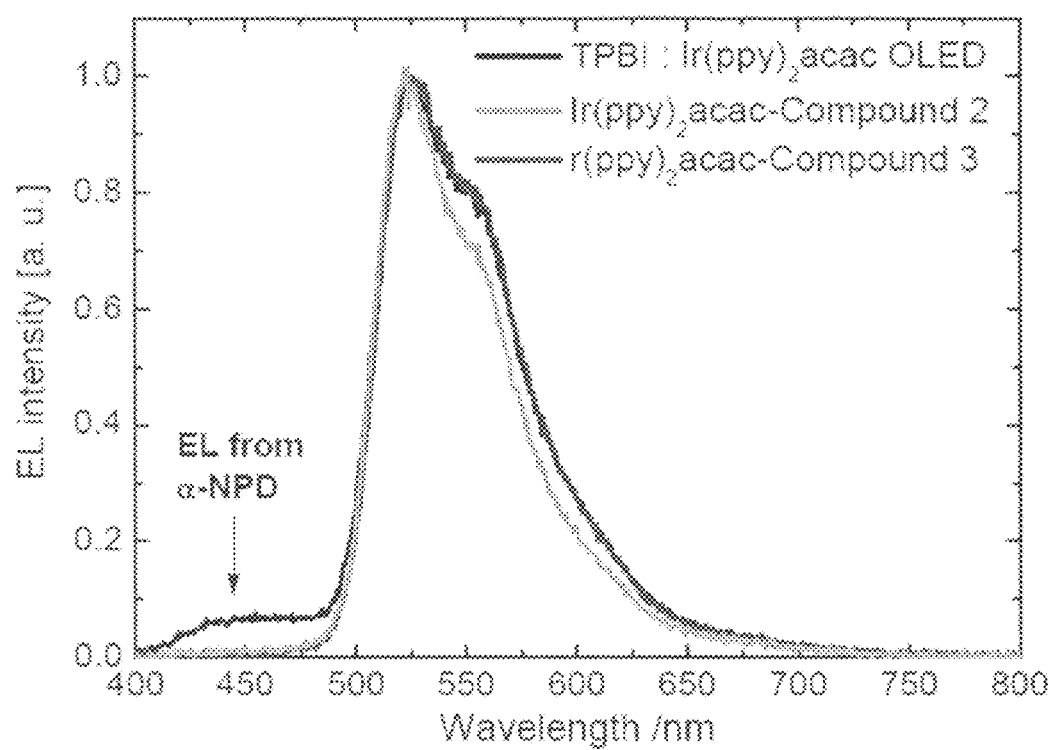
FIG. 7 shows the electroluminescence spectra of devices comprising emissive layers composed of Ir(ppy)$_2$acac and host TPBI, Compound 2 or Compound 3, respectively. Due to the improved charge-transporting properties of Compound 2 and 3, the electroluminescence spectra of the devices fabricated using Compound 2 and Compound 3 do not show electroluminescence from the hole transporting material NPD.

FIG. 7 electroluminescence spectra of devices comprising emissive layers composed of Ir(ppy)$_2$acac and host TPBI, Compound 2 or Compound 3, respectively. The device comprising TPBI: Ir(ppy)$_2$acac emissive layer does not transport holes well and the electron-hole recombination occurs on the interface of NPD and the emissive layer. Partial excitation of the NPD results in a clearly observable NPD electroluminescence. Due to the improved charge-transporting properties of Compound 2 and 3, the electroluminescence spectra of the devices fabricated using Compound 2 and Compound 3 do not show electroluminescence from the hole transporting material NPD.

Figure 8:
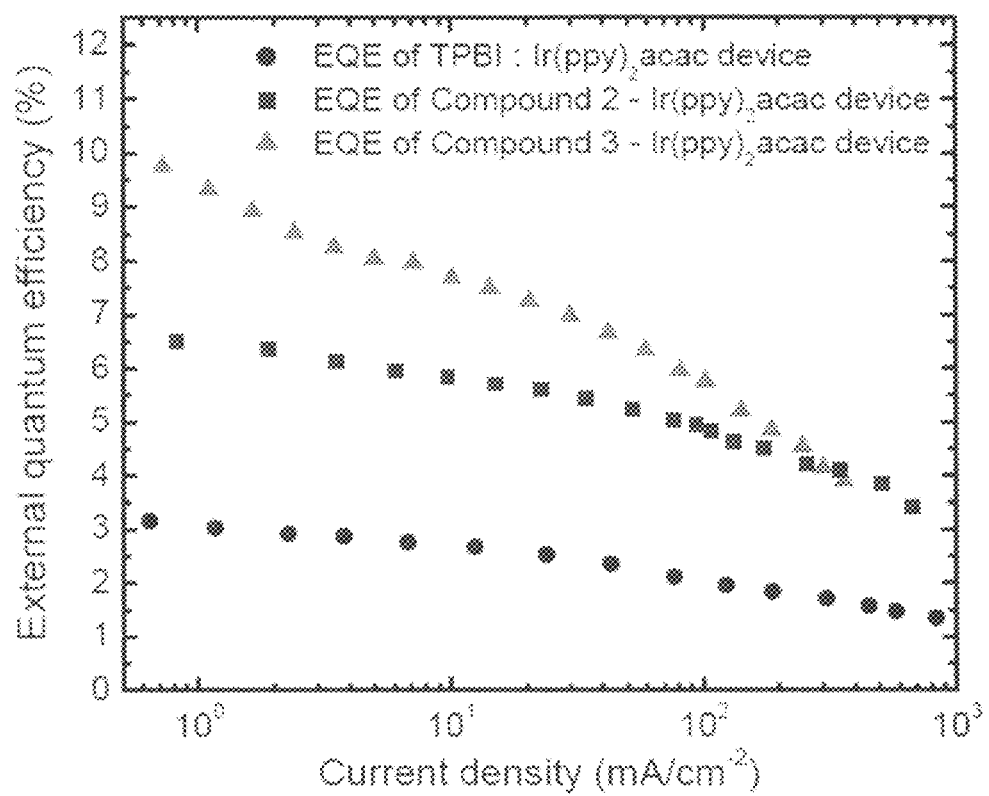
FIG. 8 shows the graph of external quantum efficiency (EQE) vs. current density in OLEDs comprising emissive layers composed of Ir(ppy)$_2$acac and host TPBI, Compound 2 or Compound 3, respectively. Due to the improved charge-transporting properties of Compound 2 and 3, the EQEs of the devices fabricated using Compound 2 or Compound 3 are significantly higher compared to the device based on the TPBI host.
Figure 9:
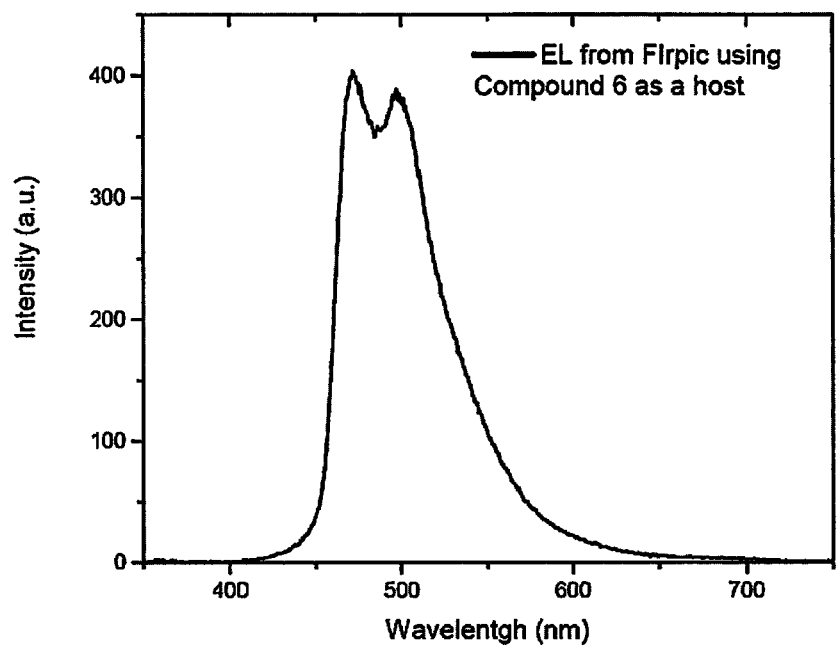
FIG. 9 shows the electroluminescence spectra of the device based on FIrpic and Compound 6.
Figure 10:
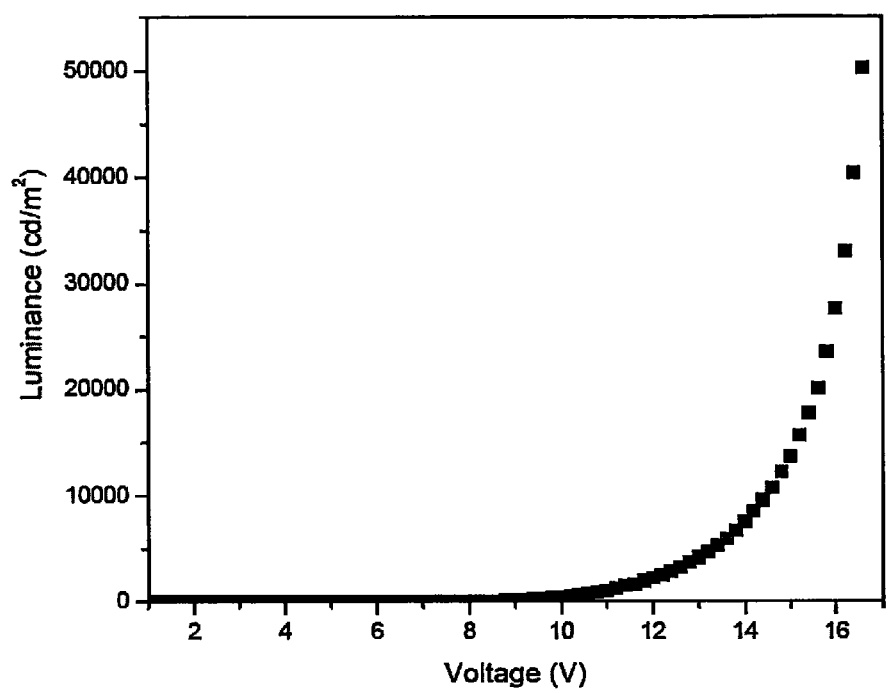
FIG. 10 shows the luminance vs. voltage curve of the corresponding OLED device based on FIrpic and Compound 6.

FIG. 8 graph of external quantum efficiency (EQE) vs. current density in OLEDs comprising emissive layers composed of Ir(ppy)$_2$acac and host TPBI, Compound 2 and Compound 3, respectively. Due to the improved charge-transporting properties of Compound 2 and 3, the EQEs of the devices fabricated using Compound 2 or Compound 3 are significantly higher compared to the device based on the TPBI host.

Figure 11:
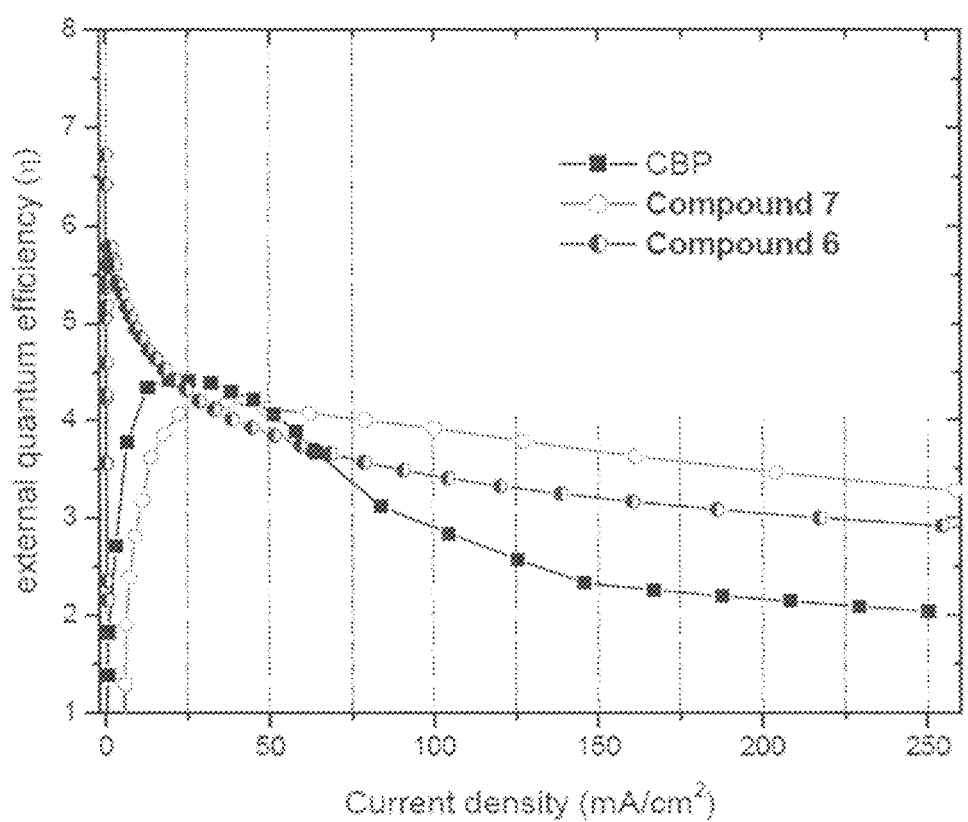
FIG. 11 shows the external quantum efficiency (EQE) vs. current density graphs the corresponding OLEDs comprising an emissive layer consisting of CPB, Compound 6, or Compound 7 doped with FIrpic.

FIG. 11 graph of external quantum efficiency (EQE) vs. current density curve of the corresponding OLEDs comprising an emissive layer consisting of CPB, Compound 6, or Compound 7 doped with FIrpic shows that the host materials 6 and 7 yield OLED devices with improved quantum efficiency. Compared to CBP, OLEDs comprising Compound 6 or Compound 7 yield significantly improved performance at higher current densities. At 100 mA/cm$_2$, the EQE for device comprising compound 7 remained close to 4.0% while that of the CBP device had already dropped to 2.9%. This difference in the EQE roll-off suggested that the Compound 6 and Compound 7 display reduced triplettriplet annihilation processes taking place in the host at high triplet exciton populations. Overall, a maximum luminance of 20,000 cd/m$_2$ was obtained for the device based on Compound 6 at a current density of 250 mA/cm$_2$.

Embodiments of the present invention are also further elucidated through additional information provided in Appendix A hereto.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art. While the invention has been illustrated and described as embodied in an organic light-emitting device, it is not intended to be limited to the details shown, since various modifications and structural changes may be made without departing in any way from the spirit of the present invention, as reflected in the claims that are incorporated into the disclosure.

What is claimed is:

1. A material having the structure:

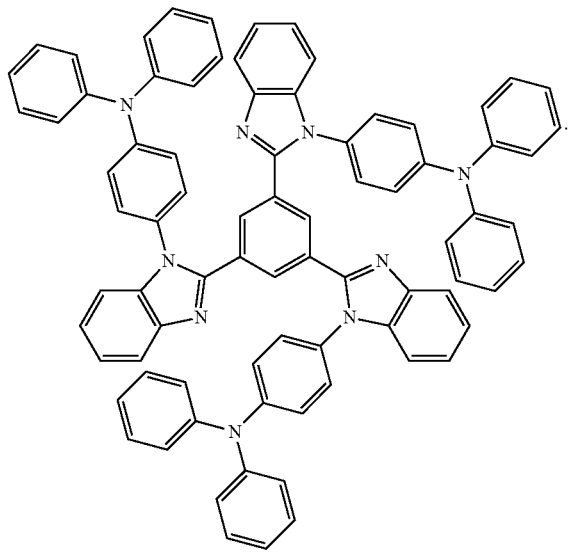 [SMILES: c1ccc(N(c2ccccc2)c2ccc(-n3c(-c4cc(-c5nc6ccccc6n5-c5ccc(N(c6ccccc6)c6ccccc6)cc5)cc(-c5nc6ccccc6n5-c5ccc(N(c6ccccc6)c6ccccc6)cc5)c4)nc4ccccc43)cc2)cc1]

2. An emissive layer comprising material according to claim 1.

3. An emissive layer comprising material according to claim 1 and a dopant.

4. A material having the structure:

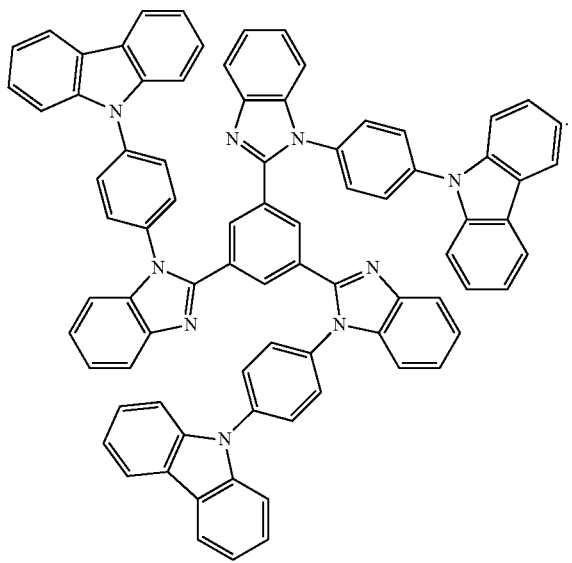 [SMILES: c1ccc2c(c1)nc(-c1cc(-c3nc4ccccc4n3-c3ccc(-n4c5ccccc5c5ccccc54)cc3)cc(-c3nc4ccccc4n3-c3ccc(-n4c5ccccc5c5ccccc54)cc3)c1)n2-c1ccc(-n2c3ccccc3c3ccccc32)cc1]

5. An emissive layer comprising material according to claim 4.

6. An emissive layer comprising material according to claim 4 and a dopant.

7. An organic light emitting device, comprising: (a) an anode; (b) a cathode; and (c) an emissive layer disposed between the anode and the cathode, the emissive layer comprising material having the structure:

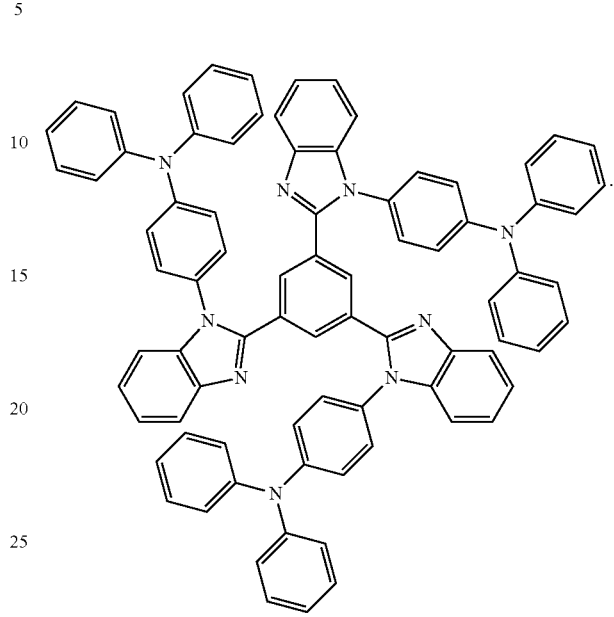

8. An organic light emitting device, comprising: (a) an anode; (b) a cathode; and (c) an emissive layer disposed between the anode and the cathode, the emissive layer, comprising material having the structure:

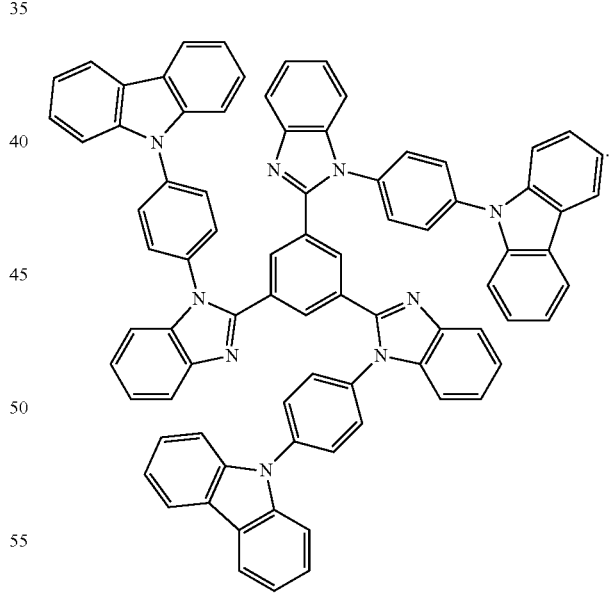

* * * * *